US012654010B2

(12) United States Patent
Venkatasubramanian et al.

(10) Patent No.: US 12,654,010 B2
(45) Date of Patent: Jun. 16, 2026

(54) INDUCTIVE LINK ARRANGEMENT

(71) Applicant: COCHLEAR LTD, Macquarie University (AU)

(72) Inventors: Arun Venkatasubramanian, Boston, MA (US); Rangarajan Jegadeesan, Singapore (SG); Rostislav Anatolievich Lemdiasov, Boston, MA (US)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 18/277,960

(22) PCT Filed: Nov. 7, 2022

(86) PCT No.: PCT/AU2022/051332
§ 371 (c)(1),
(2) Date: Aug. 18, 2023

(87) PCT Pub. No.: WO2023/154975
PCT Pub. Date: Aug. 24, 2023

(65) Prior Publication Data
US 2025/0073466 A1        Mar. 6, 2025

Related U.S. Application Data

(60) Provisional application No. 63/355,956, filed on Jun. 27, 2022, provisional application No. 63/312,363, filed on Feb. 21, 2022.

(51) Int. Cl.
*A61N 1/36* (2006.01)
*A61N 1/05* (2006.01)
(Continued)

(52) U.S. Cl.
CPC ....... *A61N 1/36038* (2017.08); *A61N 1/0541* (2013.01); *H02J 50/10* (2016.02);
(Continued)

(58) Field of Classification Search
CPC ... A61N 1/36038; A61N 1/3787; H02J 50/10; H04B 5/263; H04B 5/266; H04B 5/43; H04B 5/79; H04R 25/554
See application file for complete search history.

(56) References Cited

U.S. PATENT DOCUMENTS

| 5,991,664 A | 11/1999 | Seligman | |
|---|---|---|---|
| 11,303,160 B2 * | 4/2022 | Haerinia | ................. H02J 50/10 |

(Continued)

FOREIGN PATENT DOCUMENTS

| WO | 2017136767 A1 | 8/2017 |
|---|---|---|
| WO | 2020115721 A1 | 6/2020 |

OTHER PUBLICATIONS

Yao, Y., et al., "Simultaneous Wireless Power and Data Transfer: A Comprehensive Review," IEEE Transactions on Power Electronics, vol. 37, No. 3, Mar. 2022, 18 pages.
(Continued)

*Primary Examiner* — Catherine M Voorhees
(74) *Attorney, Agent, or Firm* — Edell, Shapiro & Finnan, LLC

(57) ABSTRACT

The present disclosure relates to an inductive coil arrangement for a transcutaneous inductive link arrangement, to devices incorporating the inductive coil arrangement and to a method of transmitting power and data using the inductive coil arrangement.

20 Claims, 13 Drawing Sheets

(51) Int. Cl.

| | |
|---|---|
| *H02J 50/10* | (2016.01) |
| *H04B 5/26* | (2024.01) |
| *H04B 5/43* | (2024.01) |
| *H04B 5/79* | (2024.01) |
| *H04R 25/00* | (2006.01) |

(52) U.S. Cl.
   CPC ............. *H04B 5/263* (2024.01); *H04B 5/266* (2024.01); *H04B 5/43* (2024.01); *H04B 5/79* (2024.01); *H04R 25/554* (2013.01)

(56) References Cited

U.S. PATENT DOCUMENTS

| | | | | |
|---|---|---|---|---|
| 2008/0027513 | A1* | 1/2008 | Carbunaru | ........... A61N 1/3787 607/2 |
| 2011/0106210 | A1 | 5/2011 | Meskens | |
| 2013/0265144 | A1 | 10/2013 | Banna et al. | |
| 2014/0062213 | A1* | 3/2014 | Wheatley, III | ........ H02J 50/402 307/104 |
| 2015/0372532 | A1* | 12/2015 | Hatanaka | .................. H02J 7/04 320/108 |
| 2017/0062932 | A1* | 3/2017 | Foster | ...................... H01Q 1/38 |
| 2020/0359550 | A1 | 11/2020 | Tran et al. | |
| 2020/0374638 | A1* | 11/2020 | Oplinger | .............. H04R 25/606 |
| 2022/0377472 | A1* | 11/2022 | McSweeney | ........ H04R 25/505 |
| 2023/0233850 | A1* | 7/2023 | Mauger | .................. A61N 1/327 604/20 |

OTHER PUBLICATIONS

Extended European Search Report for counterpart European Application No. 22926347.0, mailed Dec. 5, 2025, 9 pages.

* cited by examiner

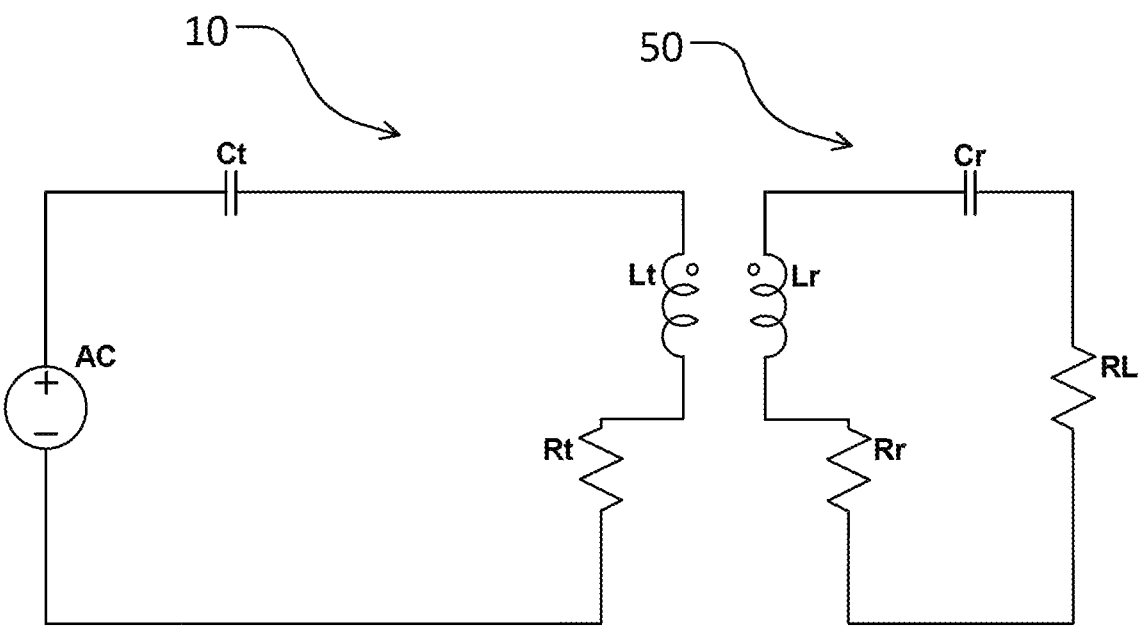
Figure 3
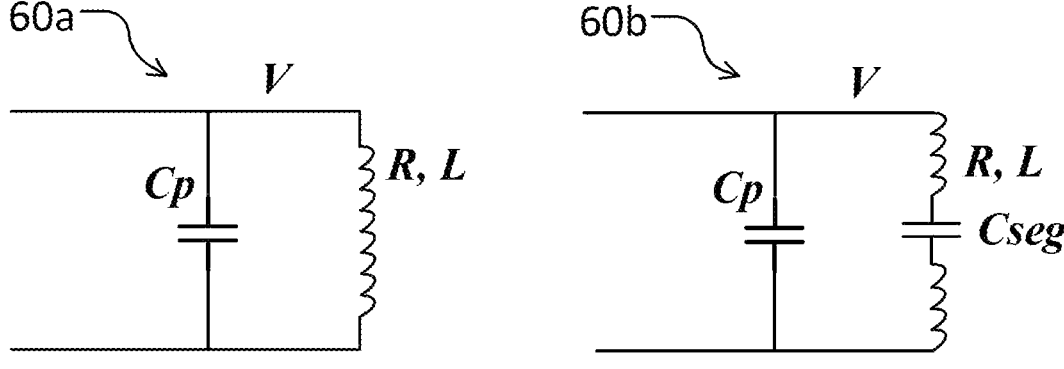
Figure 4a                                              Figure 4b 410          420

400

510

520

500

810

820

Power Coil
Coup[ling

710

720

Communications
Coil Coupling $$\phi = \sin^{-1}\left(\frac{d}{2r}\right)$$

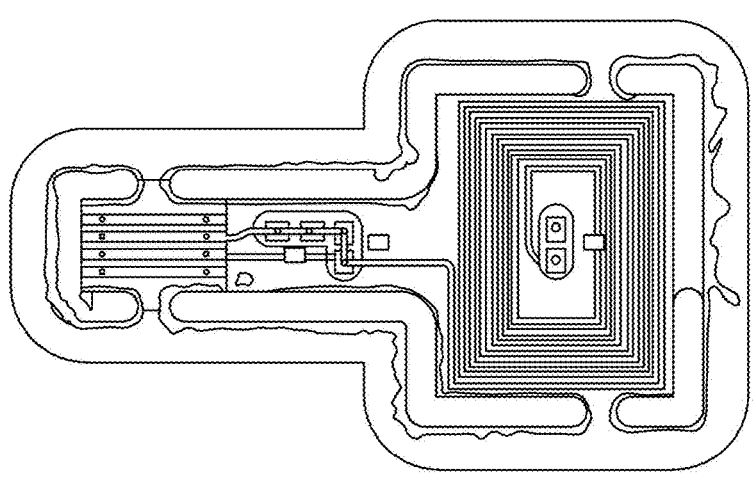
Figure 16
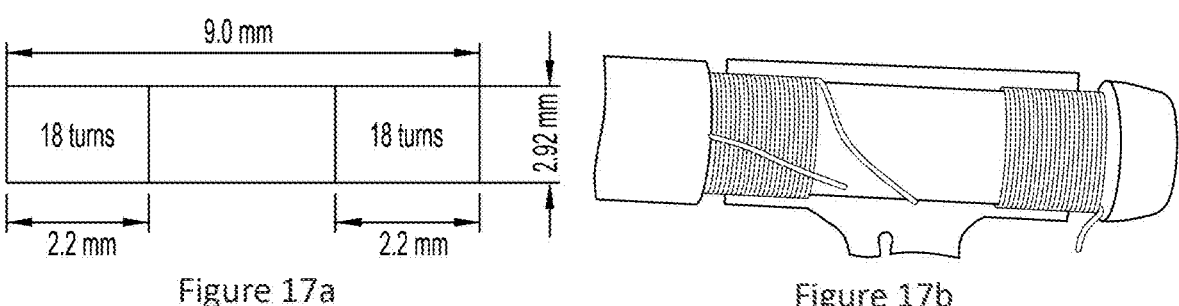
Figure 17a
Figure 17b
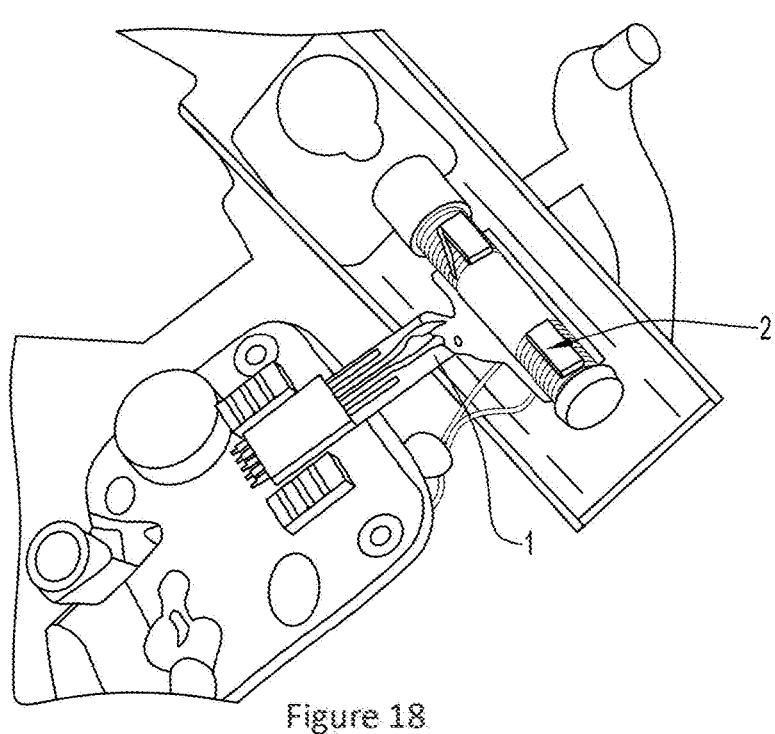
Figure 18

CRX

PRX

INDUCTIVE LINK ARRANGEMENT

CROSS REFERENCE TO RELATED APPLICATIONS

This application is a U.S. national phase of International Patent Application No. PCT/AU2022/051332 filed Nov. 7, 2022, which claims the benefit of U.S. Provisional Application No. 63/312,363 filed Feb. 21, 2022, and U.S. Provisional Application No. 63/355,956 filed Jun. 27, 2022, each of which is hereby incorporated by reference in its entirety.

TECHNICAL FIELD

The present disclosure relates to an inductive coil arrangement useful for a transcutaneous inductive link arrangement, to devices incorporating the inductive link arrangement and to a method of transmitting power and data over the inductive link arrangement. In particular, the present disclosure relates to an inductive coil arrangement being used in the context of a cochlear implant. However, the inductive coil arrangement may be useful in other medical implant applications.

BACKGROUND

Cochlear implants transmit sound information from an external wearable device (sound processor) to an implant via a transcutaneous link. This transcutaneous link enables data and power to be transferred across the skin without the need for any break in the tissue which is an infection risk. The transcutaneous link can be implemented using various technologies, including radio frequency (RF), capacitive, or ultrasonic. To date the main mechanism or technology is inductive as it provides the lowest power with the highest efficiency given the constraints on size, weight, and the regulatory standards applicable to medical devices and more specifically active implantable medical devices (AIMD).

Conventional cochlear implants typically include both external and internal components, in particular an external sound processor and an implantable receiver/stimulator. The external sound processor conventionally takes the form of a "behind the ear" (BTE) sound processor. When an inductive link is used for transcutaneous transfer of electrical power and data signals from the sound processor to the cochlear implant, the transfer conventionally takes place via an external transmitter coil provided in the sound processor and an internal receiver coil provided in the cochlear implant. The inductive link arrangement is located on the side of a patient's head and the transmitter coil is typically held in place relative to the receiver coil using permanent magnets.

More recently, inductive coil arrangements have been proposed in which the transmitter coil is provided in the ear canal. This is advantageous because it allows the coil at the receiver stimulator to be surgically placed closer to the outer ear than in the conventional systems in which the transmitter and receiver coils are located on the side of the head. However, the ear canal is a small space and challenges with this arrangement include getting enough power across the inductive link to power the implanted receiver stimulator and transmission of data with sufficient integrity. Known coil arrangements use a single coil to transmit both power and data to the implanted receiver stimulator. These tend to sacrifice data transmission integrity to achieve a high-power transfer efficiency. There is therefore a need to provide an improved arrangement.

SUMMARY

According to an aspect of the disclosure, an inductive coil arrangement for delivering a power signal and a communication signal over a transcutaneous inductive link, the inductive coil arrangement comprises:

a power signal transmitter coil for transmitting a power signal;

a communication signal transmitter coil for transmitting a communication signal;

a power signal receiver coil for receiving the power signal from the power signal transmitter coil; and a communication signal receiver coil for receiving the communication signal from the communication signal transmitter coil, wherein, in order to enable suitable delivery of the power signal and of the communication signal over the transcutaneous inductive link, the power signal transmitter coil is magnetically decoupled from the communication signal transmitter coil, the power signal receiver coil is magnetically decoupled from the communication signal receiver coil, the power signal transmitter coil is magnetically coupled to the power signal receiver coil and the communication signal transmitter coil is magnetically coupled to the communication signal receiver coil.

According to an aspect the disclosure, there is provided an inductive coil arrangement having the features set out above, when used to deliver a power signal and a communication signal over a transcutaneous inductive link.

According to an aspect of the disclosure, an implantable medical system comprises the inductive coil arrangement. The system may comprise an external (non-implantable) component comprising the power signal transmitter coil and the communication signal transmitter coil, and a component that in use will be implanted comprising the power signal receiver coil and the communication signal receiver coil.

It is possible that the implantable medical system may comprise more than one such inductive coil arrangement.

According to another aspect of the disclosure, a cochlear implant system comprises the inductive coil arrangement. In this aspect the cochlear implant system comprises an external sound processor comprising the power signal transmitter coil and the communication signal transmitter coil, and an implantable receiver/stimulator comprising the power signal receiver coil and the communication signal receiver coil.

According to another aspect of the disclosure, the external sound processor may be provided in an earbud for insertion into the ear canal of a patient. Thus, according to this aspect, an earbud comprises the power signal transmitter coil and the communication signal transmitter coil. Related to this aspect, an implantable receiver/stimulator is adapted to be implanted at a suitable location relative to the earbud when the earbud is positioned in the ear canal of a patient. The implantable receiver/stimulator will comprise the power signal receiver coil and the communication signal receiver coil. In these various aspects respective coils will be configured to establish in use the power and data communication linkages described.

According to another aspect, a method of transmitting a power signal and a communication signal over a transcutaneous inductive comprises providing the inductive coil arrangement for a transcutaneous inductive link arrangement and transmitting a power signal from the power signal transmitter coil to the power signal receiver coil and transmitting a communication signal from the communication signal transmitter coil to the communication signal receiver coil.

BRIEF DESCRIPTION OF DRAWINGS

The present disclosure is illustrated with reference to the accompanying non-limiting drawings in which:

FIG. 3 is a typical schematic diagram of a wireless power transfer system between a transmitter coil and a receiver coil;

FIG. 4 is a schematic of (a) an un-segmented coil and (b) a segmented coil;

FIG. 16 is a photograph showing a power signal transmission coil provided on a flexible printed circuit board;

FIG. 17*a* is a schematic showing a communication signal transmission coil and FIG. 17*b* is a photograph of same;

FIG. 18 is a photograph showing an arrangement of a power signal transmission coil and a communication signal transmission coil;

DETAILED DESCRIPTION

Figure 1:
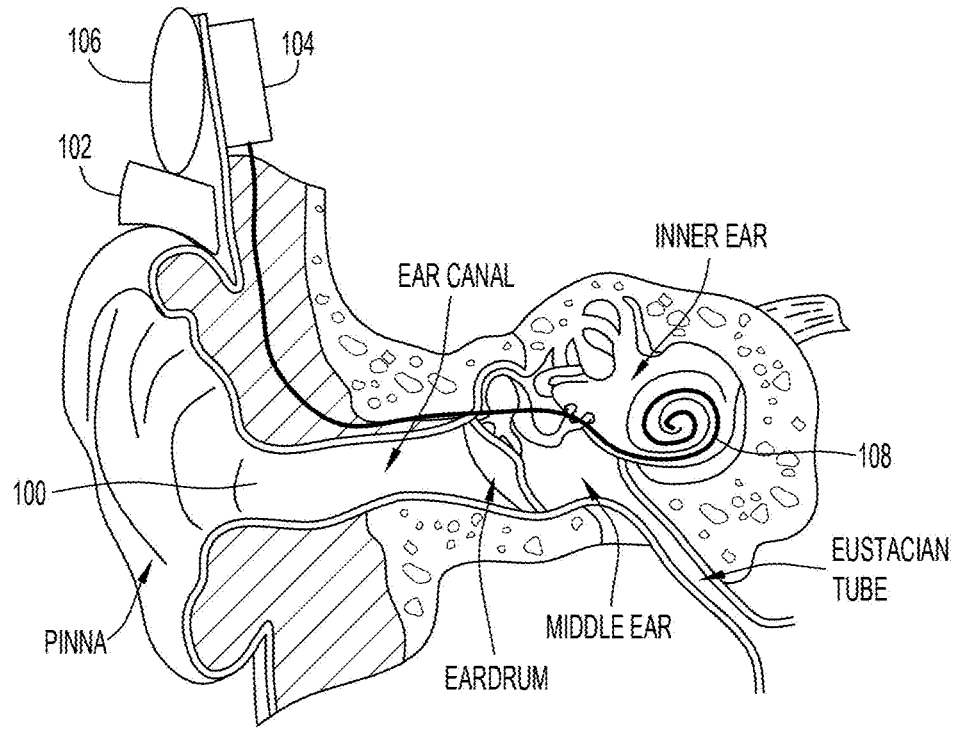
FIG. 1 is a schematic representation of a conventional arrangement for a cochlear implant system.

In accordance with the present disclosure there is provided an inductive coil arrangement that may be provided for establishing, and used for establishing a transcutaneous inductive link. The inductive coil arrangement comprises a power signal transmitter coil and a communication signal transmitter coil on one side of a cutaneous interface, and a power signal receiver coil and a communication signal receiver coil on the other side of the cutaneous interface. The power signal transmitter coil is provided for transmitting a power signal over the transcutaneous inductive link, and the communication signal transmitter coil is provided for transmitting a communication signal (data) over the transcutaneous inductive link. Correspondingly, the power signal receiver coil is provided for receiving the power signal from the power signal transmitter coil over the transcutaneous inductive link, and the communication signal receiver coil is provided for receiving the communication signal from the communication signal transmitter coil over the transcutaneous inductive link.

In accordance with the present disclosure, effective and efficient power and communications links may be established by providing coil arrangements that in use achieve suitable coupling of matched pairs (power signal transmitter coil to power signal receiver coil: communication signal transmitter coil to communication signal receiver coil) and decoupling of un-matched pairs (power signal transmitter coil to communication signal transmitter coil: power signal receiver coil to communication signal receiver coil). According to this arrangement power signals and communication signals may be delivered over a transcutaneous communications link using independent power signal transmitter/receiver coils and communication signal transmitter/receiver coils.

It will be appreciated that the required coupling and decoupling of the various coils will be established when the inductive coil arrangement is being used for signal communication over a cutaneous interface, and aspects of the disclosure relate to such active use. Aspects of the disclosure also relate to providing respective transmitter and receiver coils for establishing the inductive coil arrangement. In this case coils may be suitably provided in an external (non-implantable) component and in an implantable component, in use these components being in power and data communication with each other. Typically, the transmitter coils are provided in the external component and the receiver coils provided in the implantable component. Other configurations are however possible.

To achieve magnetic coupling the matched coils pairs may be positioned relative to each other to maximize the total magnetic flux from respective transmitter coils to respective receiver coils.

To achieve magnetic decoupling the unmatched coils may be positioned relative to each other so that the total magnetic flux between the coils is zero. This may be done by overlapping the coils. One of the coils may be provided in a "FIG. 8" configuration with the other coil overlapping a part of it.

It is also possible to achieve decoupling when the two coils are not overlapping by providing a segmentation capacitor, i.e. the coils share a common capacitor. The decoupling effect may be adjusted by varying the value of the common capacitor.

The inductive coil arrangements are configured to provide for transmission of power from the power signal transmitter coil to the power signal receiver coil over a first inductive link, and transmission of a communication signal from the communication signal transmitter coil to the communication signal receiver coil over a second (separate) inductive link. In practice, the inductive coil arrangement may be configured to provide bi-directional communication between the communication signal transmitter coil and the communication signal receiver coil, and/or between the power signal transmitter coil and the power signal receiver coil. Bi-directional communication may be important, for example to allow diagnostic checks to be run. In the context of bi-directional communication, what have been referred to above as receiver coils will have the capability for signal transmission also.

Power to be transmitted from the power transmitter coil to the power receiver coil will usually originate from a battery provided, and this may be provided in a housing with the transmitter coils. The nature of data to be communicated as between the communication signal transmitter coil and the communication signal receiver coil will vary based on field of use. For example, when used as part of a cochlear implant it will be necessary to communicate data received from an acoustic source such as a microphone. In embodiments data to be communicated may originate from another form of acoustic source, such as one or more piezoelectric devices that are configured to generate electrical signals in response to incident sound.

For effective and efficient transmission of power and communication signals, it is important that respective transmitter coils are magnetically decoupled from each other and that respective receiver coils are magnetically decoupled from each other to a suitable extent. Basically, this means that the transmitter coils and the receiver coils do not interfere with each other to a degree such that the inductive link becomes unsuitable for power and communication signals transmission in the particular context of use. Some magnetic coupling of unmatched pairs and/or magnetic decoupling of matched pairs may be tolerated but this would need to be assessed considering various factors such as the signal strength and integrity required for effective operation, the nature of the cutaneous interface etc.

Achieving the requisite extent of magnetic coupling and decoupling may be particularly challenging when the transmitter coils and the receiver coils are provided in very close proximity to each other, as would be the case when there are dimensional constraints based on the intended use. For example, when the power signal and communication signal transmitter coils are provided in an earbud for the ear canal of a patient, the available volume will usually be less than 2000 mm$^3$.

In accordance with the present disclosure suitable magnetic decoupling may be achieved by one or more of geometrical, spatial and/or electrical features associated with the respective transmitter and/or receiver coils. This is discussed in more detail below with reference to various embodiments. It is to be understood that the embodiments may be employed individually or in any combination to achieve and/or optimise the desired effect with respect to magnetic decoupling. Embodiments described with reference to transmitter coils may also be employed in relation to receiver coils. The same or different embodiments/configurations may be adopted as between transmitter coils and receiver coils.

A variety of coil designs may be used in accordance with the present disclosure. For example, planar (flat) spiral coils may be used. These may be circular or non-circular (e.g., square or rectangular) in form. For example, the coil may be formed as a trace of a suitable material (e.g., copper) on a substrate such as a circuit board. It is also possible to use a planar coil that has been deformed by folding or bending to adopt a particular configuration. The use of a curved planar coil may be beneficial in various embodiments. This may be required for suitable placement of coils adjacent one another when the available volume is small. The use of a flexible circuit board as substrate may be useful in this regard.

In another embodiment the coil may be formed by winding wire (e.g., copper wire) around a suitable former to produce a 3-dimensional winding. The winding may be circular or non-circular (e.g., square or rectangular) in design. The same or different coil designs may be used as between the various coils employed. Depending on the nature/structure of the former used an air-core 3-dimensional winding may be produced.

The coils may be made of a non-ferrite material, such as copper. Depending on design the coil may comprise a winding of wire. It is also possible to produce a planar coil by stamping from a sheet of material. As noted, a planar coil design may also be formed as a trace of a suitable material on a rigid or flexible printed circuit board.

The communication signal transmitter coil and the power signal transmitter coil may be arranged in an at least partially overlapping spatial relationship. One benefit of this is that it allows the coils to be used in volume restricted spaces, for example in an earbud. Depending on coil design and dimensions, the communication signal transmitter coil and the power signal transmitter coil may substantially overlap, or they may fully overlap. For example, depending on radii of curvature it is possible to position a curved planar coil so that it is adjacent to and overlapping the exterior surface of a cylindrical coil. The extent of overlap will also be determined by the axial length of the cylindrical coil and the corresponding dimension of the curved planar coil. In an embodiment the power signal transmitter coil has a planar curved shape, and the communication signal transmitter coil has a generally cylindrical shape. An embodiment with this type of arrangement is discussed below with reference to FIGS. 5 and 6. Example 1 refers to this type of arrangement.

In an embodiment, respective receiver coils are planar coils arranged parallel to one another in a partially overlapping spatial relationship. An embodiment of this type of arrangement is discussed below with reference to FIG. 7.

In an embodiment the communication signal receiver coil may be arranged within the perimeter of the power signal receiver coil, or vice versa. For example, the receiver coils are air-core (3-dimensional) coils arranged with respective central axes orthogonally to one another and in an overlapping spatial relationship, whereby the communication signal receiver coil is positioned within the perimeter defined by the power signal receiver coil, or vice versa. An embodiment of this type of arrangement is discussed below with reference to FIG. 8.

In an embodiment the communication signal transmitter coil and the power signal transmitter coil are arranged in an at least partially overlapping spatial relationship, and the central axis of the communication signal transmitter coil is substantially parallel to or tilted at an angle with respect to the central axis of the power signal transmitter coil. The communication signal transmitter coil may be a circular planar coil and the power signal transmitter coil may be a planar curved coil that has a curvature that complements a portion of the circumference of the circular communication signal transmitter coil to allow the power signal transmitter coil to overlap the communication signal transmitter coil at least partially. Magnetic coupling between the two coils may be reduced/minimised by tilting the communication signal transmitter coil at an angle from the orthogonal with respect to a longitudinal axis of the power signal transmitter coil. An embodiment of this type of arrangement is discussed below with reference to FIGS. 9 and 10a. With this type of arrangement the relative position of the coils may also be adjusted to minimise magnetic coupling. This is discussed in more detail with respect to an embodiment shown in FIG. 11a.

In the same way, the power signal receiver coil and the communication signal receiver coil may be arranged parallel with one another in an at least partially overlapping spatial arrangement. Further, the power signal receiver coil and the communication signal receiver coil may be arranged to overlap by an overlap distance. The overlap distance may be adjusted to reduce magnetic coupling as between the coils.

It has been observed that when an RF coil is excited, not only is there a current in the coil, but also an accumulation of electrical charges in the coil wiring. These charges cause an electrical field between the charges. Interaction of the electric field with nearby tissue can lead to an unwanted and significant rise in coil resistance. To avoid that segmentation capacitors may be introduced. For example, the wiring of the coil may be divided into roughly equidistant intervals and segmentation capacitor(s) positioned there. The value of the segmentation capacitor(s) is roughly $N/(\omega^2 L)$ in which N is the number of windings in the coil, L is inductance and $\omega$ is angular frequency. In practice, the value should be somewhat higher, because we want the coil to look capacitive to be able to tune and match it.

Accordingly, in an embodiment the power signal transmitter coil and/or the communication signal transmitter coil may include one or more segmentation capacitors. Additionally, or alternatively, the communication signal receiver coil and/or the power signal receiver coil may include one or more segmentation capacitors. When used one or more segmentation capacitors may be included between coil windings or transmission loops of respective coils. As an example of this, the communication signal transmitter coil may comprise a first plurality of wire loops and a second plurality of wire loops arranged in series, wherein the first plurality of wire loops and the second plurality of wire loops are capacitively coupled and arranged in spaced relationship with one another.

The communication signal receiver coil may have a longitudinal dimension, and the first plurality of wire loops and the second plurality of wire loops of the communication signal transmitter coil may be arranged at a distance from one another that is approximately equal to or greater than the longitudinal dimension of the communication signal receiving coil. An embodiment of this is discussed in more detail with respect to FIGS. 14 and 15.

The inductive coil arrangements may also comprise signal conditioning electronics associated with the power signal receiving coil and the communication signal receiving coil and adapted for decoupling power signal interference from the communicated signal.

In an embodiment the power signal transmitter coil may be configured to transmit a power signal to the power signal receiver coil at a frequency that is approximately two to three times higher than a frequency at which the communication signal transmitter coil is configured to transmit the communication signal to the communication signal receiver coil. A large difference in frequency between respective transmitted signals has been found to avoid the power signal from going into circuitry used for receipt of the communication signal and to avoid the communication signal from going into circuitry used for receipt of the power signal.

In another embodiment the power signal transmitter coil may be configured to transmit a power signal to the power signal receiver coil at a frequency that is separated by at least 10 MHz from the frequency at which the communication signal transmitter coil is configured to transmit a communication signal to the communication signal receiver coil. For example, the power signal transmitter coil may be configured to transmit a power signal to the power signal receiver coil at a frequency of about 27.12 MHz, and the communication signal transmitter coil may be configured to transmit a communication signal at a frequency of between about 10 MHz and 13.56 MHz.

It will be apparent to the skilled person that two or more of the disclosed embodiments of the inductive link arrangement may be combined where appropriate. For example, the communication signal transmitter coil and the power signal transmitter coil of an inductive link arrangement may be arranged in an at least partially overlapping spatial relationship and may also include one or more segmentation capacitors.

In the context of cochlear implants, the present disclosure may be employed in the context of a sound processor in the form of an earbud for insertion into an ear canal and a suitably corresponding implant. However, it is also possible that the present disclosure may be employed to provide a cochlear implant where the sound processor is provided as a behind above the ear component with a suitable near mastoid bone implant. Of course, a cochlear implant (or other form of implantable medical system) will include a variety of other components to achieve the desired functionality. One skilled in the art would be familiar with such componentry and how it may be implemented in the context of the present disclosure.

It is also possible that the inductive link arrangement of the present disclosure may be employed in other forms of implantable medical systems. For example, wireless power transmission and data communication using an inductive link have been demonstrated for various biomedical applications including visual prosthesis, neuromuscular and nerve stimulators, cardiac pacemakers/defibrillators, deep-brain stimulators, spinal-cord stimulators, brain-machine interfaces, gastrointestinal microsystems, and capsule endoscopy.

A schematic representation of a conventional cochlear implant arrangement is shown in FIG. 1. This typically includes an external sound processor 102 and an implantable receiver/stimulator 104. The receiver/stimulator 104 is implanted at the side of the head of the patient. The sound processor 102 sits behind the ear of the patient. Electrical power and data signals are transferred from the sound processor 102 to the receiver/stimulator 104 via an external transmitter coil 106. The external transmitter coil is located over the receiver/stimulator 104 on the outside of the head and is held in place by permanent magnets.

Conventional transcutaneous links utilise a single link to transmit power and data. The link is accomplished by generating an RF carrier signal that can transmit power efficiently across the skin/tissue of the patient, and then an AM modulated signal is applied to the carrier signal to create a way to encode 1s and 0s to the signal so that data can be transferred.

This is an elegant solution as a single link meets the dual requirements of transferring power and data signals to the implanted component. However, the solution compromises system efficiency. For example, to generate modulated RF for transfer of the data signal results in a reduction in the total power transferred, as any time a '0' is transmitted there is a reduction in the RF carrier signal being sent across the link and therefore a reduction in power.

The sound processor 102 is required to deliver power continuously so that the receiver/stimulator 104 can continuously stimulate the cochlea via an electrode array 108. Breaks or power drops in this stimulation can cause noises known as pops or bangs, or in a worst case, pain and/or tissue/cell damage can occur due to this lack of consistent power across the transcutaneous link.

The conventional cochlear implant is required to operate completely from the external sound processor 102. Furthermore, there is a limit on the level of power that can be transferred across the tissue interface due to regulatory safety limits based on skin absorption rates (SAR). This tissue interface can vary in thickness in different patients. Therefore, the inductive link must be able to send data across a range of tissue (skin flap) thicknesses without loss of data or reduced power delivery whilst staying below safety limits. The skin flap thicknesses can vary between 2 mm-15+mm across a patient population.

The cochlear implant is dependent on the sound processor 102 and the ability for the RF inductive link to meet the power, thickness and SAR requirements. This typically results in a compromised system when the inductive link shares power and data at the same time, as now the system needs to be tuned to transfer power across a wide range of skin thicknesses, with a high level of efficiency, but also effectively and reliably transmit data from the sound processor 102 to the implant 104.

An inductive system is typically utilised for the transcutaneous power and data transfer as it is a circuit that can be tuned to optimise the competing requirements of efficiency of power transfer, bandwidth, and data integrity. The optimum conditions are determined by a Q factor of the circuit in which the Q, or Quality factor is a dimensionless number used to describe the performance of the system. The higher the Q number, the less losses in the system. The lower the Q number, the more losses in the system, however the wider the tolerance on the bandwidth and skin flap thickness achievable. Thus, for a system where data are being transferred across a shared link where efficiency is critical, and so is data transfer, the Q factor is tuned to an optimum number that allows the inductive link to meet the multiple requirements demanded of the inductive system.

As the cochlear implant is reliant on power from the external sound processor 102, and the external sound processor 102 has a limited power supply itself, the implant capabilities, stimulation strategies, processing, etc, are greatly dominated by the power that can be transferred to it. If the implant power consumption is too high the external battery will deplete too quickly, or the link is unable to transfer enough power to keep the implant within its operating voltage (voltage compliance). Increasing the power across the transcutaneous link is not a viable option if a battery of the external sound processor 102 does not then last its required life, or if the inductive link causes heating of the skin. This places a limit on the amount of functionality that the implant can provide.

The external RF transmitter coil 106 attached to or associated with the sound processor 102 and an RF receiver coil at implanted receiver/stimulator 104 are typically coiled wire or similar, and of a large enough diameter to maximise the efficiency of the power link whilst allowing data transfer. The RF transmitter coil 106 can be 30+mm in diameter and resides behind the ear on the mastoid bone where a coil of that size can sit on a relatively flat surface to allow maximal coupling between the respective transmitter and receiver coils. Any curvature of the coils, lateral or angular misalignment, or too large a gap between the coils can significantly reduce power and/or data transfer. The area behind the ear is chosen as it provides a relatively low-risk surgical site, but also meets the requirements for size, flatness, and alignment of the transmitter and receiver coils. However, as noted, the thickness of the tissue between the coils can be quite variable as between different patients. This variation in the tissue thickness can greatly impact the RF performance for both power and data. To allow for this possibility, the inductive link is typically detuned (to a lower Q factor) to allow for a wider variation in skin flap thickness, which is detrimental to the link efficiency.

As mentioned earlier, one or more magnets are used to hold the RF transmitter coil 106 onto the side of the head and provide a stable connection to the receiver coil of the receiver/stimulator 104. Magnets are a simple and effective technique to hold the transmitter coil 106 on the head, however they have a few drawbacks/side effects. A magnet impacts MRI scans by introducing a risk of adverse events from the magnet moving or tearing the skin, as well as blocking out large areas of the skull during the scan due to imaging artefacts. This is a major problem with conventional cochlear implants, especially as MRIs are now moving to higher and higher magnetic field strengths. Some manufacturers utilise a special magnet that moves the alignment of the magnetic poles to better align with the magnetic field of the MRI. Other manufacturers recommend removal of the implant magnet prior to MRI scanning. Removal necessitates a small incision in a patient's skin to remove the magnet and replace it once the scan is finished. To date, there are no commercially available cochlear implants that can operate without a magnet.

The placement of the transmitter coil 106 on the head of the patient above the mastoid bone also has a downside from a usability point of view. Placement of the transmitter coil 106 here can make it uncomfortable/hard to sleep. It can also be challenging to wear helmets, hats or head bands. Furthermore, long hair can continuously knock the coil off the head. Studies have shown that cochlear implant patients' transmitter coils 106 can become disconnected frequently during a typical day due to bumping, hair movement, thick skin flaps, etc. Each time a coil is disconnected from the receiver/stimulator 104, the sound processor 102 stops communicating, which in turn means the patient is no longer able to hear. Increasing the magnet strength is one way to combat this, however doing so can cause pain or tissue damage due to excess pressure on the tissue beneath the transmitter coil 106.

Recipients of cochlear implants are also conscious of the appearance of the external components of the device from an aesthetics point of view and would prefer not to have components visible on the side of their head. To date, no commercially available cochlear implants devices have resolved this issue. This is mainly due to the complications and requirements of the inductive link, as described above.

Figure 2:
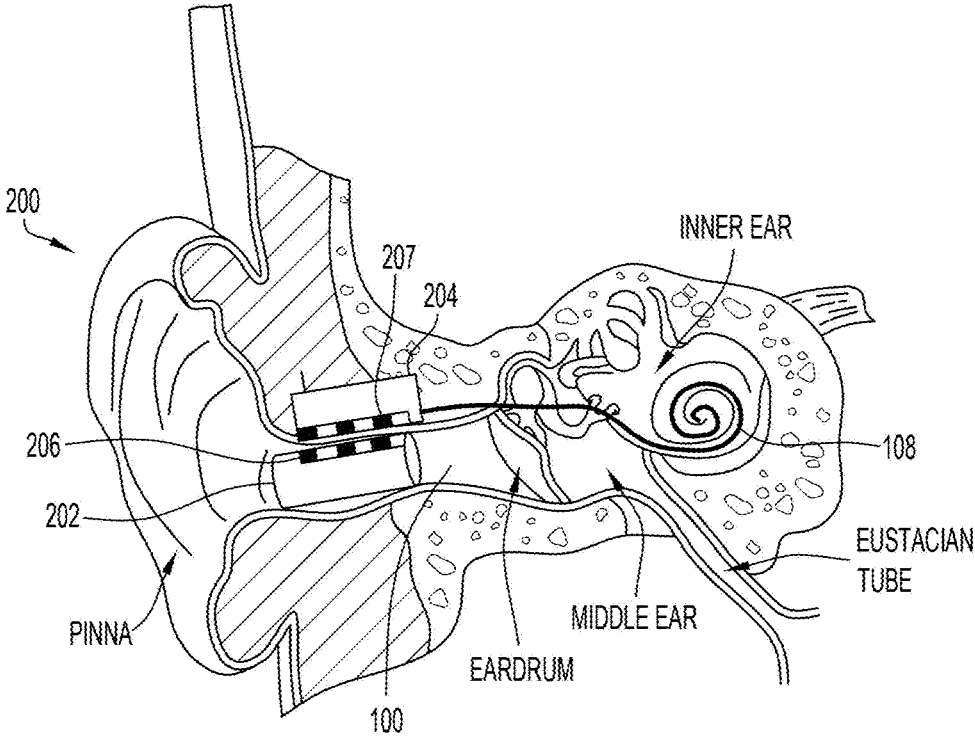
FIG. 2 is a schematic representation of an embodiment of an arrangement for a cochlear implant system in accordance with the present disclosure.

FIG. 2 shows a schematic representation of components of a cochlear implant 200 in accordance with aspects of the present disclosure in which an external sound processor 202 resides in the ear canal 100. The sound processor 202 is coupled to a receiver/stimulator 204 implanted behind the outer auditory canal (the ear canal). The receiver/stimulator 204 includes a receiver coil arrangement 207 of a transcutaneous inductive link arrangement in accordance with the disclosure. The external sound processor 202 is provided in the form of an earbud that is adapted to fit into the ear canal of the patient. The earbud also houses a transmitter coil arrangement 206 of the transcutaneous inductive link arrangement. A benefit of utilising an earbud is the outer features of the ear (concha) can hold and align the earbud without the need for a magnet. Another benefit is that skin thickness between the inner and outer auditory canals is relatively consistent across the population: typically, the skin thickness is between 3 mm to 5 mm. This allows for a more efficient tuning (higher Q factor) of the inductive link arrangement of the cochlear implant 200. This potential to achieve a higher efficiency than before is critical to the feasibility of utilising the inner and outer auditory canal for placement of the coils 206, 207 of the inductive link arrangements, as the RF transmitter and receiver coils are required to be sufficiently small that they can fit within an ear bud for location in the outer auditory canal and be implanted safely at the inner auditory canal, respectively.

One of the primary aspects of the inductive coil arrangements according to the present disclosure is the use of a dedicated coil for power signal transmission over a first inductive link and a separate dedicated coil for communication signal transmission across a second inductive link at both the earbud and the implant respectively. This arrangement implies that there are two coils that are placed in very close proximity to each other in a confined space, for example in an earbud and an implant respectively, with spatial volumes of <2000 mm³ (20 mm×20 mm×5 mm). As the operating frequencies for these inductive links range between 10 MHz and 30 MHz (λ~30,000 mm to 10,000 mm) the available volume relative to free space wavelength λ is 74e-12.

FIG. 3 shows a schematic diagram of a wireless power transfer arrangement for a one-channel magnetically coupled system. The system has a transmitter circuit 10 and a receiver circuit 50. The transmitter circuit 10 includes a transmitter coil (Lt), an AC voltage supply (AC), a resistance (Rt) and a series capacitor (Ct). The series capacitor Ct serves to cancel out the inductance of the transmitter coil Lt. Given the excitation AC voltage, this allows the current (transmitter current) flowing in the transmitter coil Lt to be maximised. The receiver circuit 50 includes a receiver coil Lr, a resistance Rr, a load resistor RL and a series capacitor Cr. The transmitter current in the transmitter coil Lt induces voltage in the receiver coil Rr. The induced voltage, in turn, causes current to flow in the receiver circuit 50 and the load resistor RL. Power dissipated in the load resistor RL is the delivered power. The power dissipated in the resistances Rt and Rr represents power loss. Efficiency of the power transfer is a ratio of the delivered power PL to the input power Pin. It is reasonable to assume that to maximise the efficiency, it is required to increase coupling between coils Lt, Lr, and to decrease the Rt and Rr resistances.

To estimate the efficiency of the power transfer we first introduce the mutual quality factor, QM, where M is the mutual inductance, and ω0 is the angular frequency:

$$Q_M = \frac{\omega_0 M}{\sqrt{R_t R_r}}$$

Secondly, skipping the derivation, the optimal value RLopt of the load resistor RL is:

$$R_L^{opt} = R_r \sqrt{1 + Q_M^2}$$

The efficiency η of the power transfer is, finally:

$$\eta = \frac{P_L}{P_{in}} = \frac{\sqrt{1 + Q_M^2} - 1}{\sqrt{1 + Q_M^2} + 1}$$

Some embodiments of the present disclosure also include segmentation capacitors Cseg with transmitter and receiver coils as shown schematically in FIG. 4b and as will be explained later. The segmentation capacitors Cseg are inserted into the wiring of the coil and in at least some embodiments are located roughly equidistantly along the wiring of the coils.

In the schematic coil diagrams of FIG. 4a and FIG. 4b, a capacitor Cp simulates the parasitic self-capacitance of the coil 60a, 60b. FIG. 4a represents an unsegmented coil 60a, whilst FIG. 4b represents a segmented coil 60b.

The reasoning for including the segmentation capacitor Cseg is as follows. To develop the required current I in the transmitter coil, the equation voltage V=(R+jωL) is applied, where L is the inductance, j is the imaginary unit and ω is the angular frequency. If we introduce the segmentation capacitor Cseg, then the voltage V becomes $$V = I\left( R + j\omega\left( L - \frac{1}{\omega^2 C_{seg}} \right) \right)$$

The value of the segmentation capacitor Cseg is chosen to reduce the visible inductance of the coil compared to the pure coil inductance L. This means that voltage V that needs to be applied to the coil would be reduced. In turn, lower voltage V means that the effect of the parasitic shunt capacitance Cp on the circuit also reduces. As this capacitance can be a source of potential loss, the introduction of the segmentation capacitor Cseg leads to reduction of losses in the circuit.

$$\left( L - \frac{1}{\omega^2 C_{seg}} \right)$$

The inclusion of segmentation capacitors lowers the voltages in the system and the electric field around the coil is also lower. This means that there is less interaction between the coil and the nearby biological tissue. The presence of the biological tissue may affect the coil in two ways: (a) it leads to increased visible resistance of the coil, (b) it leads to change in the inductance of the coil, which may shift the resonance frequency. This potentially harmful behaviour depends on proximity and position of the tissue relative to the coil. Introducing the segmentation capacitors Cseg may help to minimise these issues.

Figure 5:
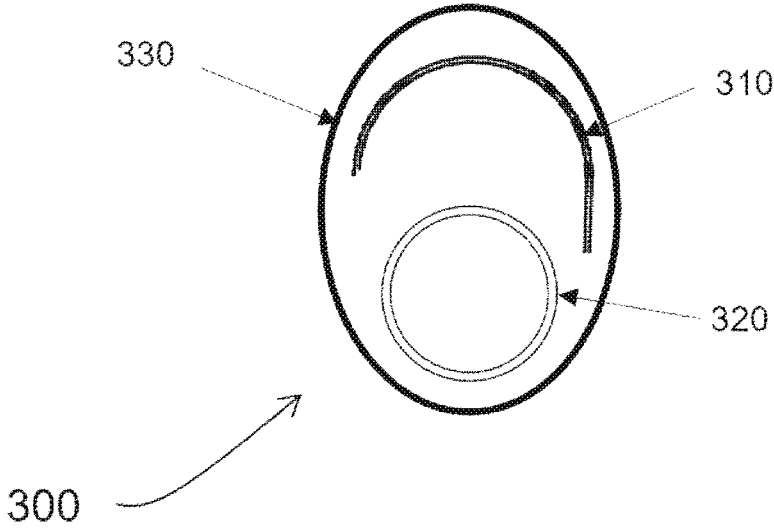
FIG. 5 is a cross-section of an earbud coil arrangement.
Figure 6:
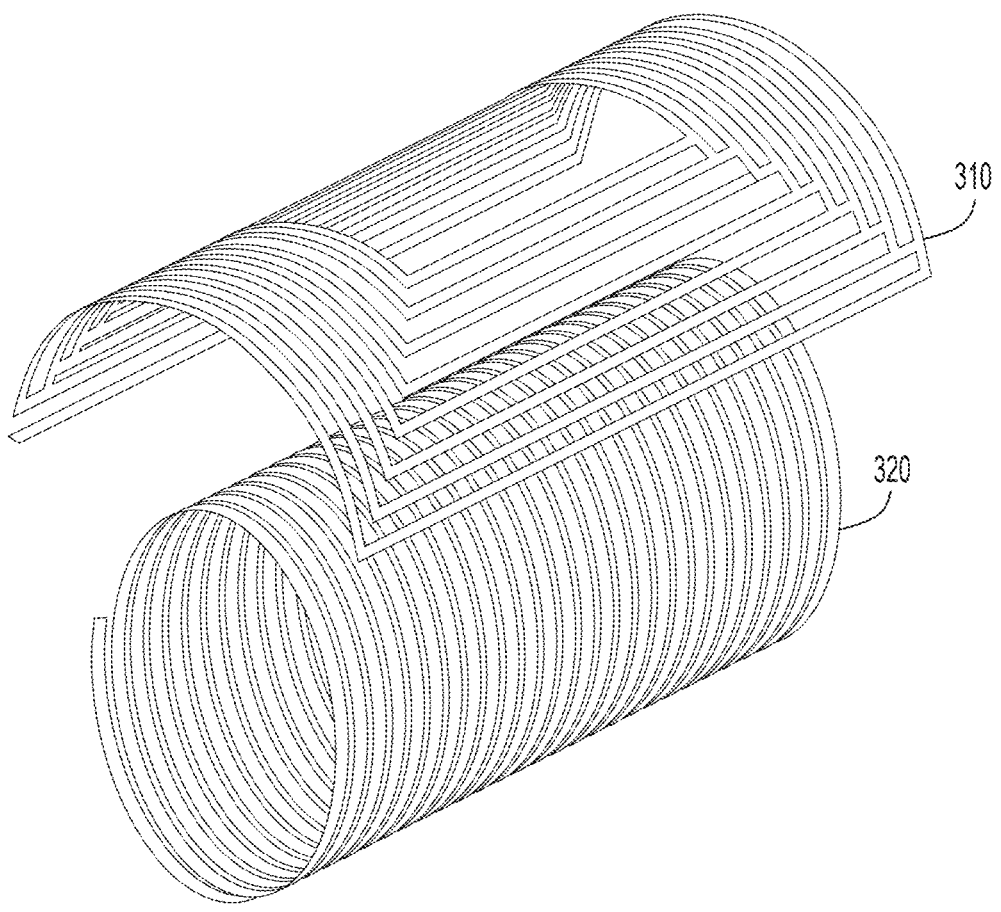
FIG. 6 is a schematic perspective view of the earbud side coil arrangement of FIG. 5.

FIG. 5 shows a front cross-sectional view of transmitter coils arrangement 300 for use in the kind of inductive link arrangement of FIG. 2. FIG. 6 shows a perspective view of the coils arrangement. In FIGS. 5 and 6, the power transmitter coil 310 may be manufactured as a flexible printed circuit board (about 8×6 mm) with spiral copper traces on top and on bottom layers. The flexible printed circuit board is bent and retained using a plastic holder (not shown). The communication signal transmitter coil is a solenoidal wire coil wound on cylindrical bobbin. The transmitter coil arrangement 300 including power signal transmitter coil 310 and separate data/communication signal transmitter coil 320 may be housed in an earbud 330 as shown in FIG. 5. For the earbud 330 to reside within the ear canal, the transmitter coils 310, 320 are sufficiently small as well as curved and cylindrical to maximise their surface area and conform to the available interior shape and volume of the ear bud 330. It is possible however that the transmitter coils 320, 330 may also be used in a behind-the ear coil arrangement rather than in an earbud.

This approach leverages the use of flexible printed circuit board materials which aid in producing consistent and automated manufacturing processes. Additionally, the use of a flexible substrate allows for production of a shaped component can conform to the required earbud design. Flexible printed circuit board materials predominantly utilise copper as a conductive material and a polyimide substrate. Whilst these materials are a good solution for the earbud side coils, they are less suitable for the implant side coils as they do not meet biocompatibility requirements. One way to overcome this would be to integrate the coils into the implant body and encapsulate them in biocompatible materials. Another solution would be to utilise more biocompatible materials such as gold, platinum, etc.

As further shown in FIG. 5, the earbud 330 has a generally oval exterior shape when viewed in cross-section. The data signal transmitter coil 320 is generally cylindrical in shape and sized to fit within a lower half of the earbud 330. The power signal transmitter coil 310 is positioned over the data signal transmitter coil 320 and comprises a planar curved coil that has a curvature to conform to the curvature of the interior of the earbud. The curvature of the power signal transmitter coil 310 also allows it to be positioned adjacent and in close proximity to the data signal transmitter coil 320. As can be seen in FIG. 5, both the data signal transmitter coil 320 and the power signal transmitter coil 310 reside within the earbud enclosure. The two coils are suitably sized and shaped so that they may be arranged in an at least partially overlapping spatial relationship. For example, they may substantially overlap or fully overlap as shown in FIG. 6.

The two coils 310 and 320 act independently of one another: the power signal transmitter coil 310 for transmitting electrical power across a first inductive link and the communication signal transmitter coil for transmitting data across a second inductive link. When current flows through the coils 310 and 320, each coil will have an associated magnetic field. The magnetic field generated by the first coil (say 310) couples with the second coil (say 320) which is either in proximity and/or partially overlapping the first coil 310 (as shown in FIG. 6). This cross coupling can cause corruption of the data signal when power is being transmitted and reduction in efficiency of the power transfer link when the data is exchanged between the bud and the implant. In accordance with the invention, the coils are designed and optimised in a manner to avoid this as far as possible. The issue of independence of the magnetic fields of the coils is also addressed in the receiver coils on the implant side of the inductive link arrangement. In the limited space available in the earbud (and on the implant side), physical distancing of the coils by several wavelengths of the standard operating frequencies is not possible given the standard operating frequencies for these inductive links range between 10 MHz and 30 MHz (λ~30,000 mm to 10,000 mm). The available area for the coils in the earbud and the implant is >1000 times smaller than the free space wavelength λ.

Figure 7:
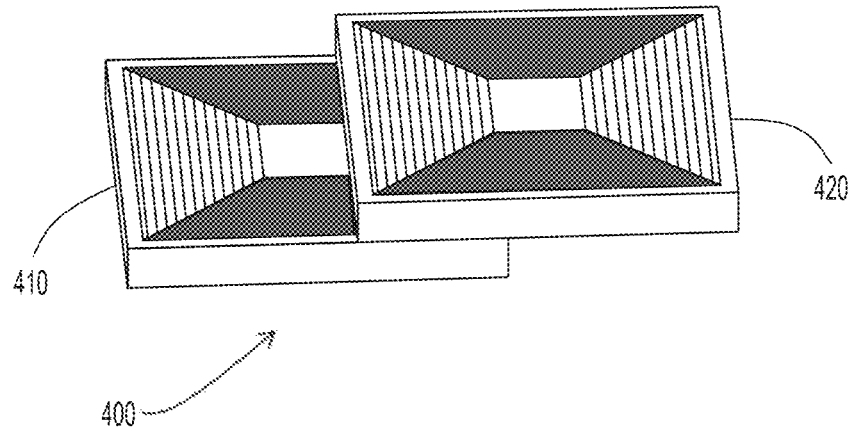
FIG. 7 is a perspective view of an implant side coil arrangement.

FIG. 7 shows a schematic perspective view of an implant side coil arrangement i.e., a receiver coil arrangement 400 for use in the inductive link arrangement of FIG. 2. In FIG. 7, the power signal receiver coil and the communication signal receiver coil are made from rigid FR-4 printed circuit boards with spiral copper traces on top and on bottom layers. The overlap between the coils is adjusted to minimise the mutual inductance between them. The receiver coil arrangement 400 has a power signal receiver coil 410 and a separate communication signal receiver coil 420. Due to the limited spatial volume available within the implant area adjacent to the outer auditory canal, the receiver coils 410, 420 are also arranged partially or fully within the same volume. In FIG. 7, the receiver coils 410, 420 are planar coils arranged parallel to one another in a partially overlapping spatial relationship. Even if there was a larger volume for the implant coils such that the overlap was not required, physical separation of the coils may not be sufficient to achieve adequate magnetic decoupling.

Figure 8:
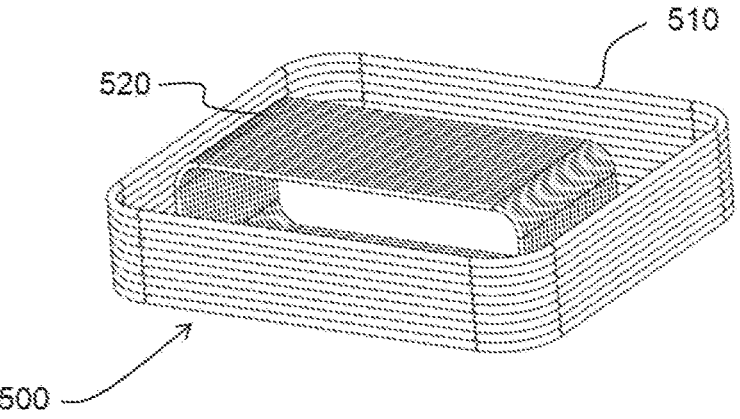
FIG. 8 is a perspective view of another implant side coil arrangement.

FIG. 8 shows an example of an alternative receiver coil arrangement 500 for use at the implant side of the inductive link arrangement of FIG. 2. In FIG. 8, the power signal receiver coil and the communication signal receiver coil are solenoidal and they are wound on rectangular bobbins. The receiver coil arrangement 500 has a power signal receiver coil 510 and a separate communication signal receiver coil 520. In this embodiment, the receiver coils 510, 520 are solenoid coils arranged orthogonally to one another in an overlapping spatial relationship, whereby the communication signal receiver coil 520 is positioned within the perimeter of the power signal receiver coil 510. Alternatively, the communication signal receiver coil 520 may be wound around the perimeter of the power signal receiver coil 510.

Optimised magnetic flux linkage coupling as between respective transmitter and receiver coils is necessary to maximise power transfer and efficiency across the respective power and data inductive links. A number of factors may impact the magnetic coupling achieved. Thus, the power transmission and receiver coils require proximity to each other to maximise magnetic flux linkage coupling. The size of the transmitter coils and the receiver coils should be closely matched and as large as possible to maximise the magnetic flux linkage. The shape of the transmitter and receiver coils is optimised to facilitate effective coupling across the tissue. For example, curvature of the power signal transmitter coil allows for a larger coil area than if the coil was flat. The size and shape of the transmitter coils also impacts the spacing and alignment of the coil positions on the implant side. The spacing and alignment of the transmitter coils is ideally aligned as much as feasible on the implant side without impacting the coupling between the power signal receiver coil and the communication signal receiver coil. In practice a combination of these factors may be trialled and adjusted in order to derive the best results for a given application, volume constraints etc.

Figure 9:
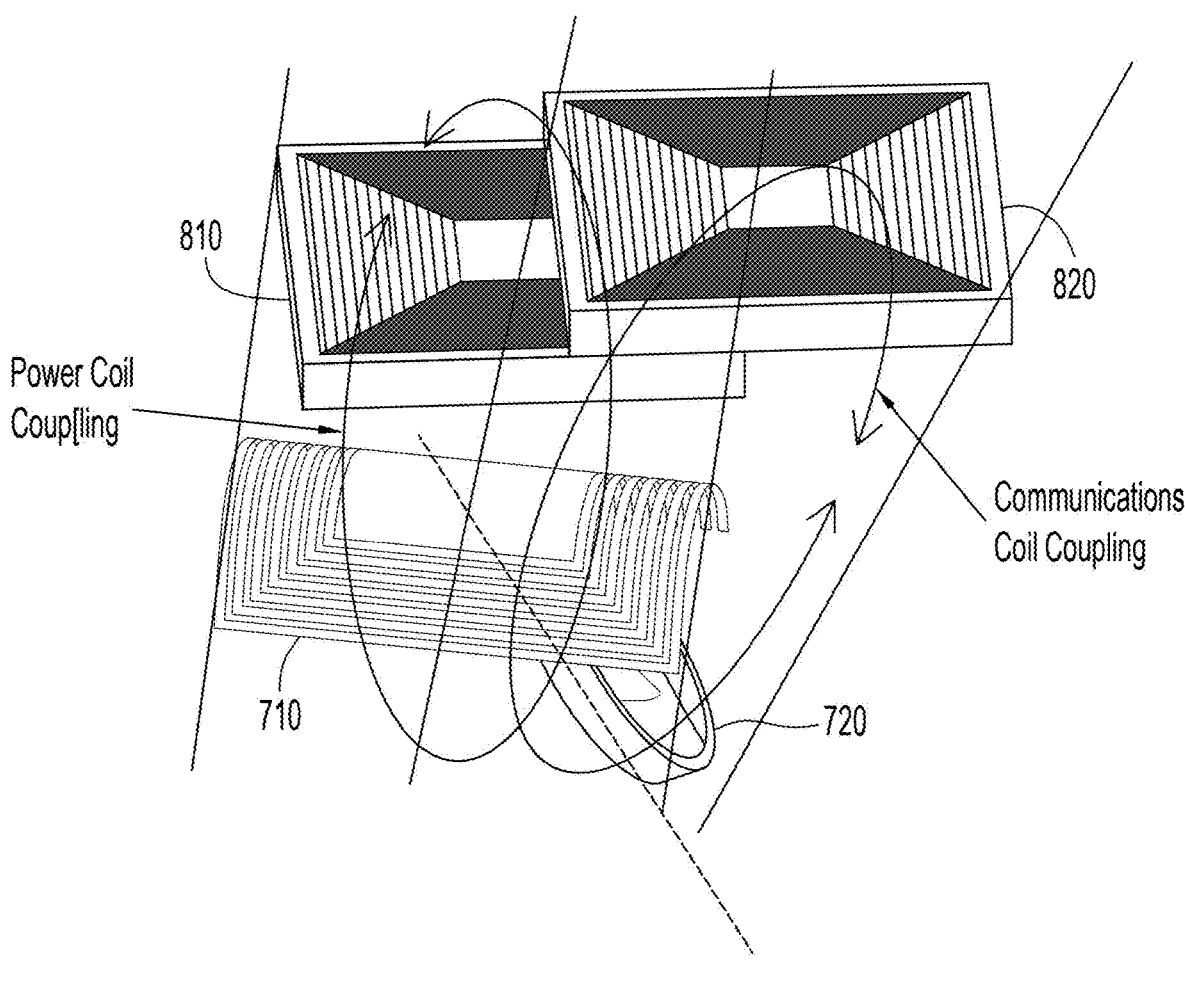
FIG. 9 is a schematic representation of magnetic coupling between power coils and communication coils of the inductive link arrangement.

Magnetic coupling between power coils and communication coils is shown schematically in FIG. 9. It is desirable to have the power signal transmitter coil 710 and the power signal receiver coil 810, as tightly coupled as possible to achieve as high a power transfer efficiency as possible, whilst minimising magnetic coupling of the communication signal transmitter coil 720 and the power signal transmitter coil 710. The communication signal transmitter coil 720 and the communication signal receiver coil 820 should be coupled together so that low error rate data communication over the transcutaneous link is achieved, whilst minimising magnetic coupling of the communication signal receiver coil 820 and the power signal receiver coil 810.

As mentioned above, the form and arrangement of the communication signal transmitter coil and the power signal transmitter coil may be optimised to maximise the magnetic flux linkage coupling to the respective receiver coils whilst minimising the magnetic coupling as between the transmitter coils. In the arrangement depicted in FIG. 9 minimisation of magnetic coupling may be achieved by tilting one coil relative to the other and/or longitudinally offsetting one coil relative to the other as described below.

Figure 10A:
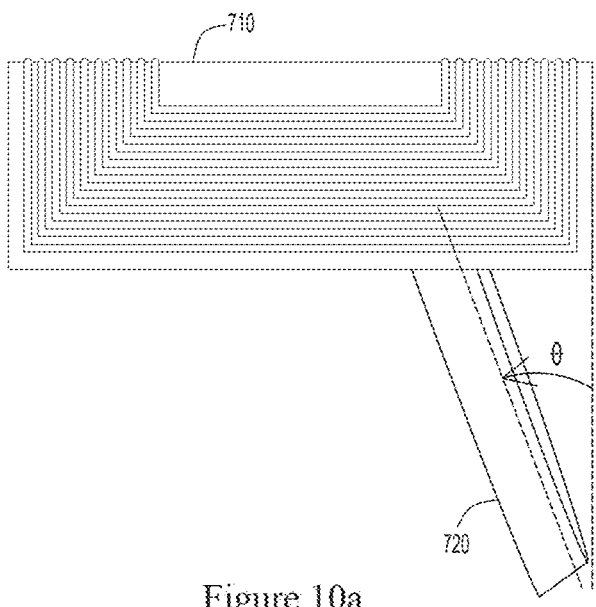
FIG. 10*a* is a schematic perspective view of the variability of an angle θ and FIG. 10*b* is a graph showing its effect on coupling factor K between two transmitter coils.
Figure 11A:
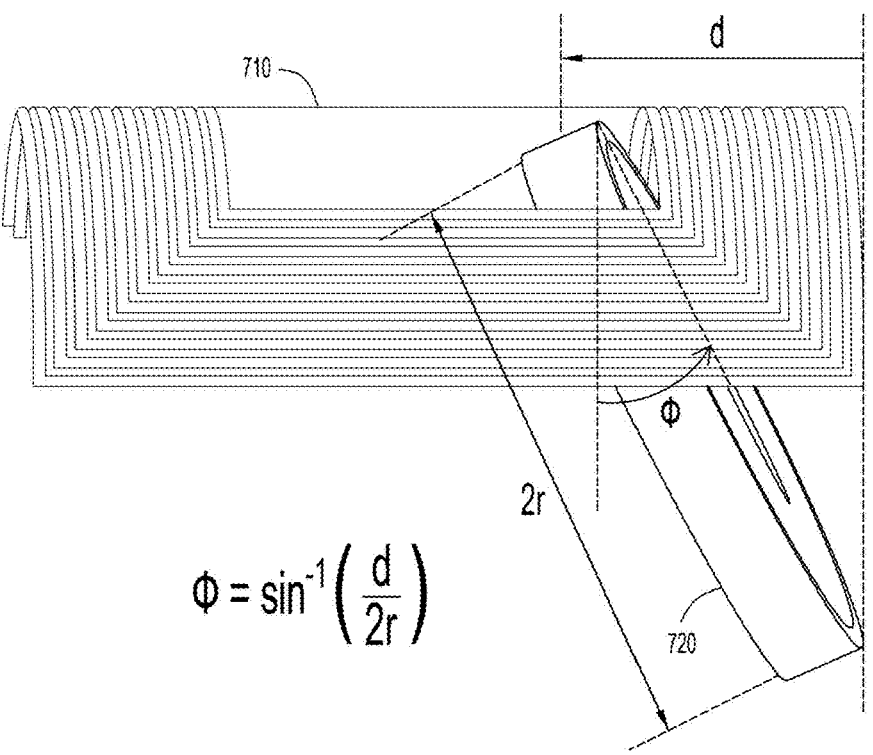
FIG. 11*a* is a schematic perspective view of the variability of an offset distance 'd' and FIG. 11*b* is a graph showing its effect on coupling factor K between two transmitter coils.

In FIGS. 9, 10a and 11a, a communication signal transmitter coil 720 is arranged in a partially overlapping spatial relationship with a power signal transmitter coil 710 so as to maximise the coil area whilst staying within the limited spatial volume of an earbud. The communication signal transmitter coil 720 is a circular planar coil. The power signal transmitter coil 710 comprises a planar curved coil that has a curvature that complements a portion of the circumference of the circular communication signal transmitter coil 720. To reduce cross coupling between the two coils, the communication signal transmitter coil 720 is tilted at an angle θ from the orthogonal with respect to a longitudinal axis X-X of the power signal transmitter coil 710 as seen in FIG. 10a. The communication signal transmitter coil 720 is tilted at its base, rotated inwardly towards the centre of the power signal transmitter coil 710. The tilt angle θ of the communication signal transmitter coil 720 is selected so that the magnetic coupling of the communication signal transmitter coil 720 is minimised in relation to the power signal transmitter coil to a sufficient degree for power and communications transmissions to occur at the same time without impacting each other.

Figure 10B:
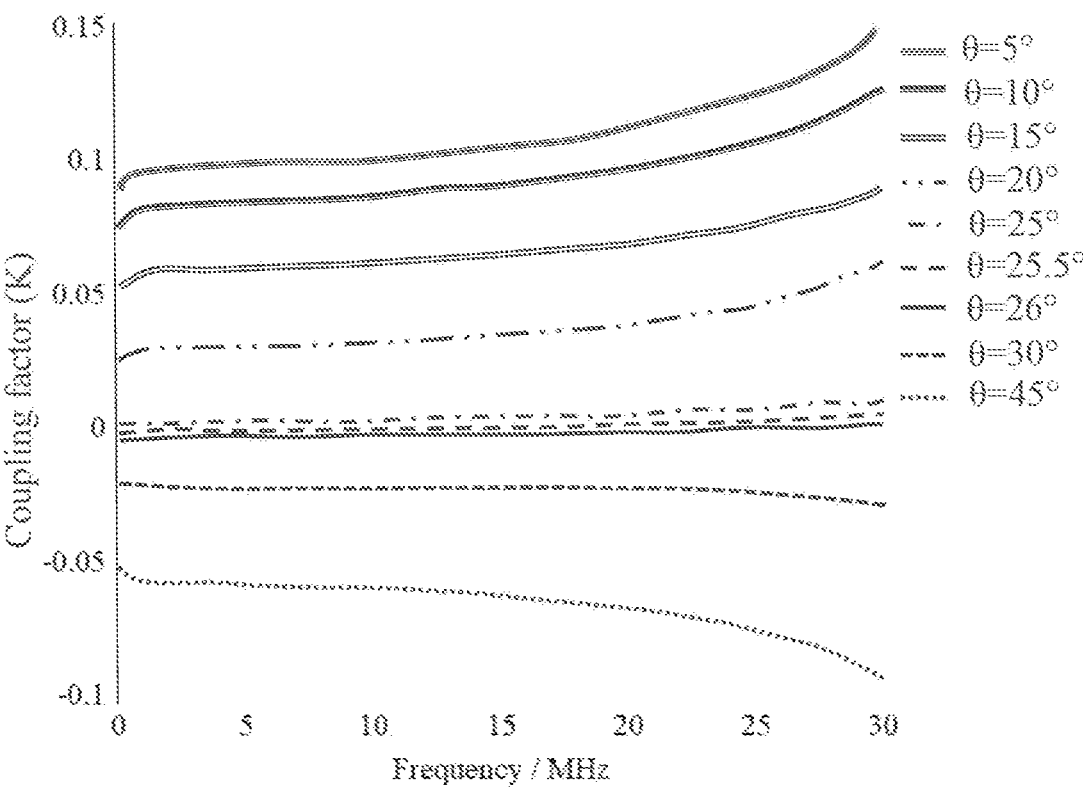

The degree of coupling between the communication signal transmitter coil 720 and the power signal transmitter coil 710 is measured using a coupling factor (K). A coupling factor K of zero or approaching zero is desired to minimise the deleterious effects of cross coupling. The tilt angle θ may be varied and the coupling factor K between the communication signal transmitter coil 720 and the power signal transmitter coil 710 determined to find the optimal angle to reduce the coupling between the two coils. As an example, for the arrangement of coils shown in FIG. 10a, the graph included as FIG. 10b shows that a tilt angle θ of between 25° to 27° from orthogonal (defined as a direction perpendicular to the plane containing the power signal transmit coil 710) is optimal. The specific configuration 25.5° from normal provides the minimum amount of coupling K. However, each individual arrangement of coils will require tuning to achieve optimum results.

Figure 11B:
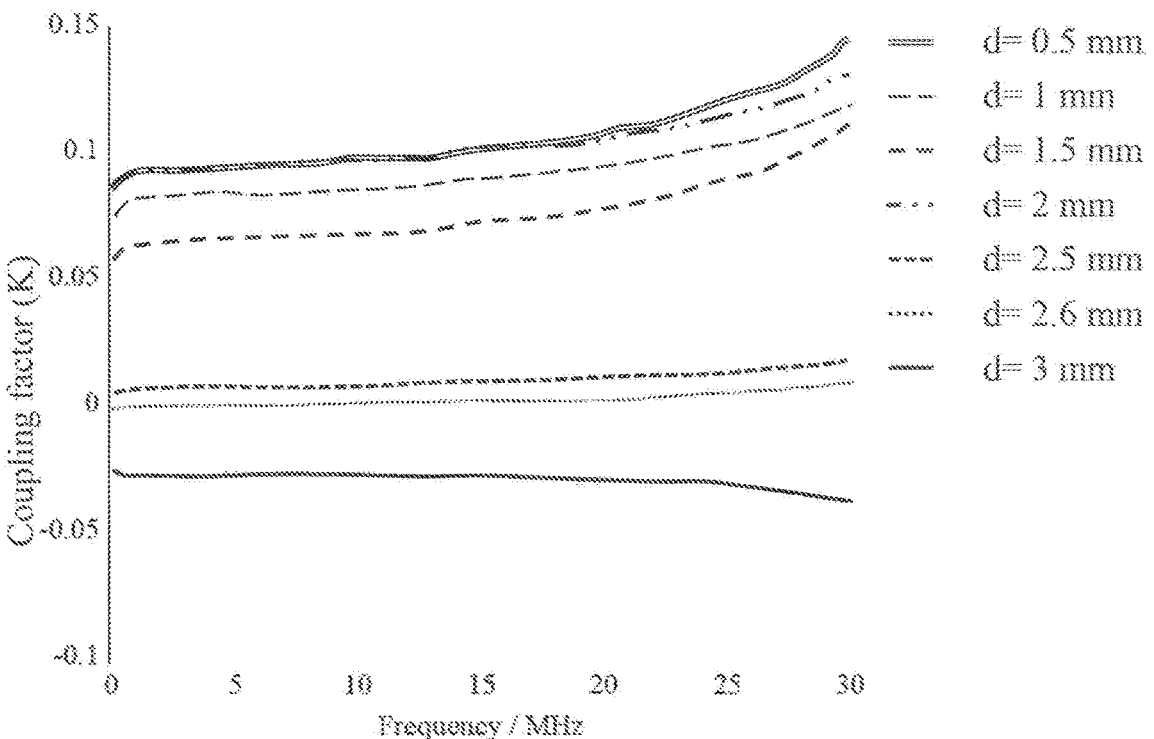

The degree of coupling (defined by the coupling factor K) can be further reduced by altering a longitudinal position or 'offset distance' of the planar communication signal transmitter coil 720 along the length of the power signal transmitter coil 710 coil. For example, the power signal transmitter coil 710 has a first curved edge 712 beneath which the base of the communication signal transmitter coil 720 is positioned. An upper portion of the communication signal transmitter coil 720 may be moved longitudinally along the underside of the planar coil 710 by an offset distance 'd' as seen in FIG. 11a. The offset distance 'd' is measured from the first curved edge 712 of the power signal transmitter coil 710 to a mid-point of the upper most surface 722 of the communication signal transmitter coil 720. Adjusting the offset distance 'd' varies the coupling factor K as illustrated in the graph included as FIG. 11b. The optimal offset distance 'd' may be between 1 mm and 3 mm, for example between 1.5 mm and 2.7 mm. For this coil arrangement, the optimal offset distance 'd' is 2.6 mm. However, each individual coil arrangement will require tuning to achieve the optimum result.

Figure 12A:
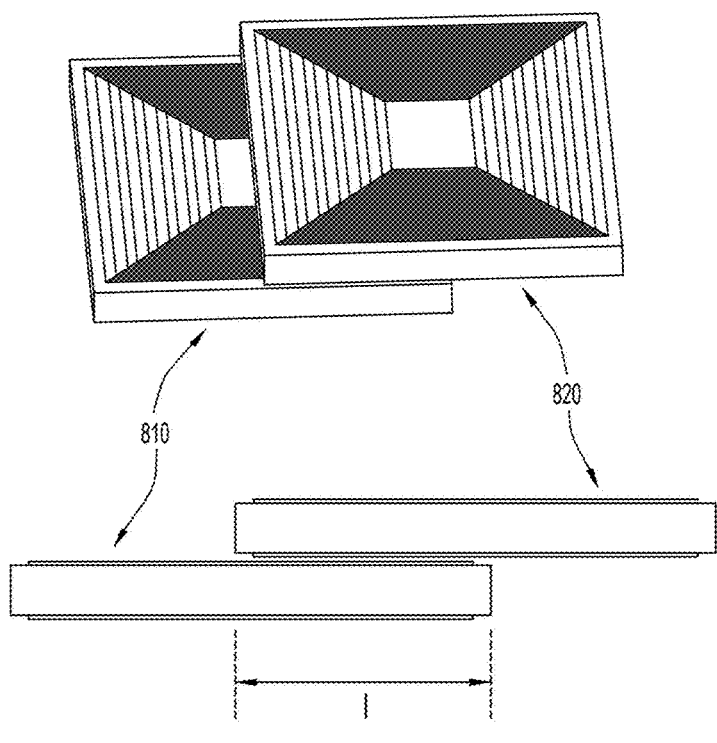
FIG. 12*a* is a schematic perspective view of the variability of an overlap distance '1' and FIG. 12*b* is a graph showing its effect on coupling factor K between two receiver coils.
Figure 12B:
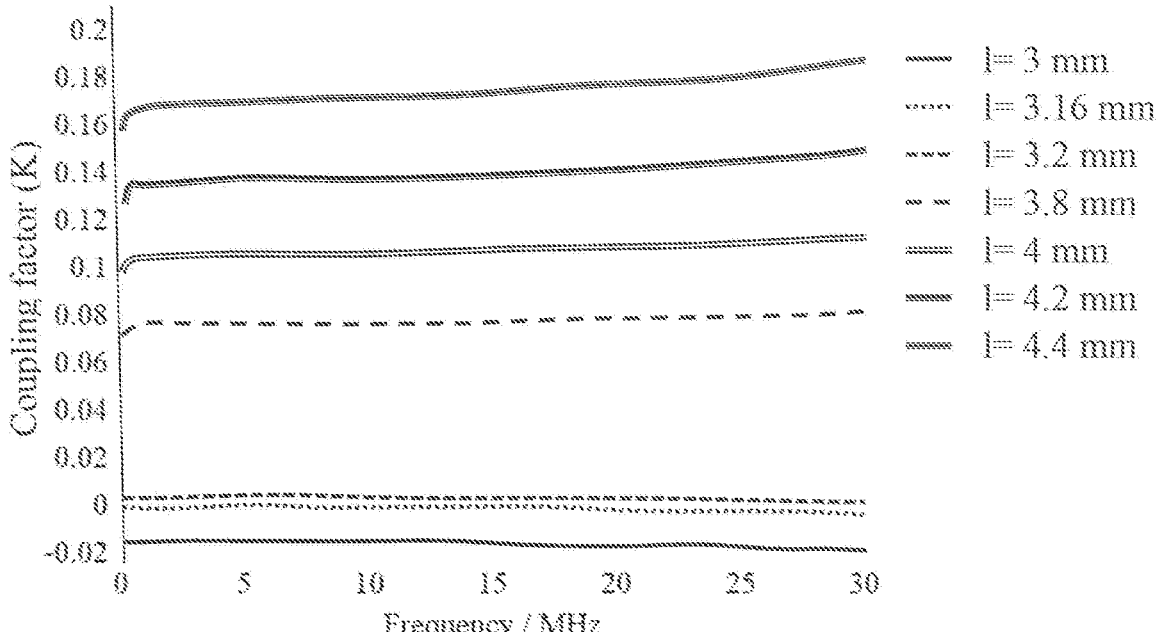

A similar tuning exercise may be undertaken to determine an optimum overlap distance 'l' for the arrangement and form of power signal receiver coil 810 and communication signal receiver coil 820 shown in FIG. 12a. The graph included as FIG. 12b indicates that the optimum overlap distance 'l' is 3.16 mm.

In an embodiment the coupling factor (coupling coefficient) between unmatched coils (i.e. between respective transmitter coils, between respective receiver coils and between power or communication signal transmission coils and communication or power signal receiver coils) is suitably low, for example less than 1%. In an embodiment, the coupling factor may be from 0.2 to 0.4%. For effective and efficient operation, the extent of coupling between the power transmission and receiver coils may be different from the extent of coupling between the communication signal transmission and receiver coils. In practice, it is likely that effective data transfer over the communication signal link may be achieved at a lower degree of coupling (i.e. lower coupling factor) than is required for effective power transfer. A fundamental requirement for the communication link to be effective is that a requisite volume of data can be transmitted with low error rate.

The operating frequencies of the power signal transmitter coil and the communication signal transmitter coil may also be adjusted to maximise decoupling of the coils whilst meeting the communications requirements for data throughput, without impacting the power consumption e.g., of the cochlear implant. Increasing the frequencies to too high a frequency may achieve better data throughput and decoupling but also increases the power consumption of the electronics, reducing the overall efficiency of the inductive links. The operating frequencies also have to be within allowable frequency bands for medical devices. In the embodiments of the present disclosure, the operating frequencies of each of the two inductive links, power and communications, is selected to be out of the frequency band of the other inductive link. It would be easy to select frequencies that are separated by decades so that the lower frequency inductive link, in this case communications, can filter out any higher frequency signal, power in this case, from the communications inductive link. However, the tuning of these circuits also needs to consider the optimal frequency for power transfer and efficiency, as well as the optimal frequency for communications bandwidth and data integrity.

Switching losses is a major factor in designing any RF system and is even more important in ultra-low power circuits such as a cochlear implant system. To minimise switching losses of the communications system, a lower frequency, of approximately 10 MHz, is selected as it is low enough to reduce switching losses without effecting the transfer rate of data. An operating frequency of lower than 10 MHz may reduce power losses but may also reduce the transfer rate of data, which may result in the communications link being unable to transfer sufficient audio signal for correct stimulation of an electrode array. The power inductive link is tuned to 27.12 MHz in some embodiments of the present disclosure, to move the frequency out of the communications frequency spectrum but also to a range where an optimum coil design/arrangement could be found given size and spacing requirements.

Figure 13:
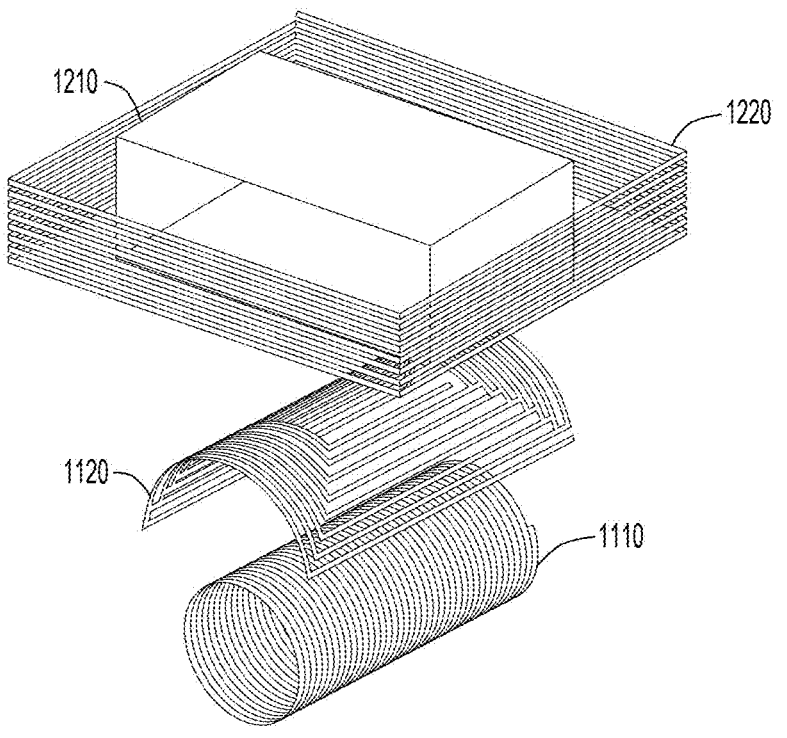
FIG. 13 is a schematic perspective view of a second embodiment of an inductive link arrangement.

An alternative embodiment of the coils of the inductive link arrangement is shown in FIG. 13. In this embodiment, each of the communication signal transmitter coil 1110, communication signal receiver coil 1220 and power signal receiver coil 1210 is provided in the form of a solenoid. Each coil is wound around a central axis and stacked or laid adjacent to the next coil. The power signal transmitter coil 1120 is a conformal printed spiral coil as in the embodiments of FIGS. 5, 6, 9, 10*a*, 11 and 13. The communication signal transmitter coil 1110 is adjacent and in close proximity to the power signal transmitter coil 1120 whereby the two coils are arranged in an at least partially overlapping spatial relationship, and wherein the central axis of the communication signal transmitter coil 1110 is substantially parallel to a central longitudinal axis of the power signal transmitter coil 1120. The communication signal receiver coil 1220 is wound orthogonally around the power signal receiver coil 1210.

Implantable coil assemblies have biocompatibility and MRI related constraints on the properties of the mechanical assemblies that can be used to make the coils. These constraints pose challenges to implementing a ferrite based solenoidal coil geometry on the implant side which can reduce the achievable magnetics efficiency below 50%, making the overall system efficiency target of this transcutaneous link untenable. To address this challenge and to achieve the required magnetics efficiency within the very constrained space envelope, some embodiments of the present disclosure utilise a unique combination of flexible printed spiral coils and a segmented solenoidal air core coil, as described below.

Figure 14:
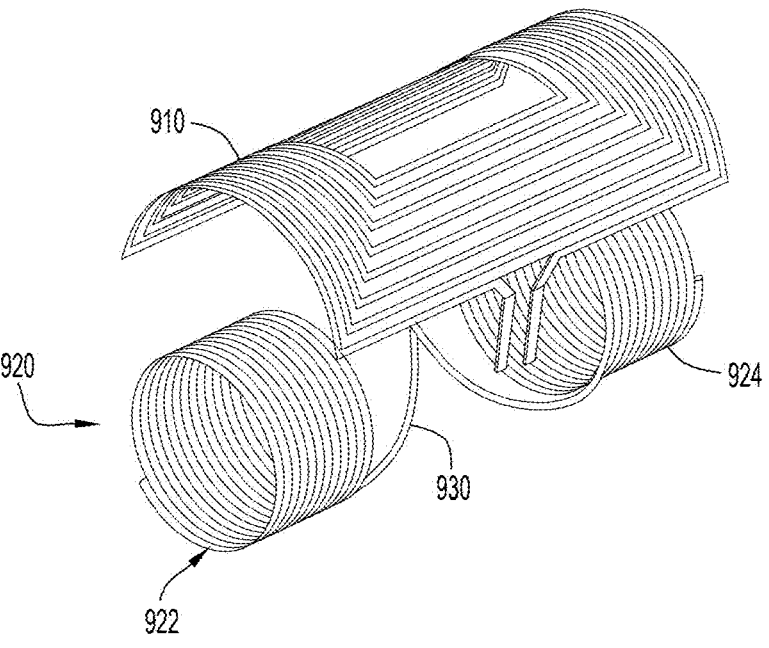
FIG. 14 is a schematic perspective view of a second embodiment of a bud side coil arrangement.
Figure 15:
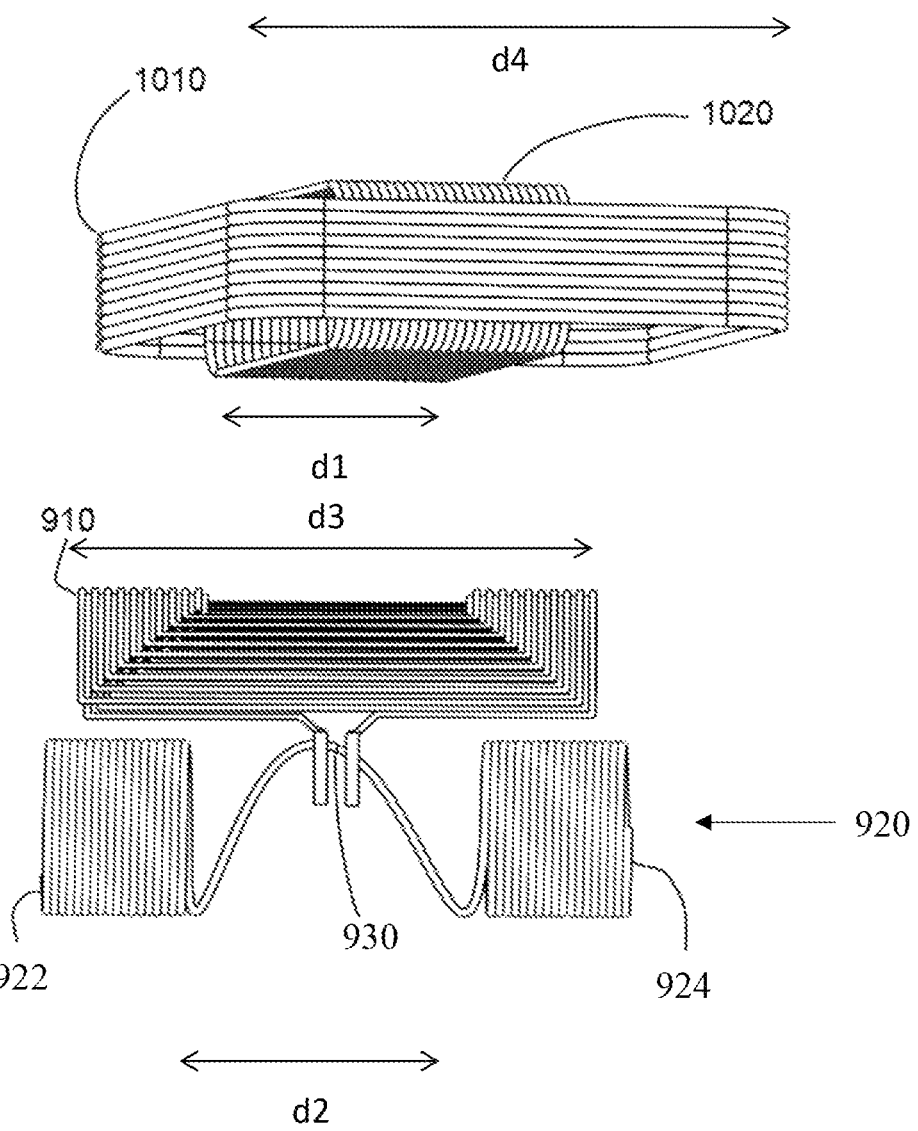
FIG. 15 is a schematic perspective view of a third embodiment of an inductive link arrangement.

FIGS. 14 and 15 show an embodiment of a communication signal transmitter coil 920 that comprises two coil windings 922, 924 separated by a segmentation capacitor 930. The communication signal transmitter coil 920 is made of two windings 922, 924, 18 turns of AWG-38 magnet wire each around a suitably shaped former/bobbin (not shown). The overall coil length is 9 mm, the diameter is 2.92 mm. The power signal receiver coil is wound using 10 turns of AWG-34 magnet wire. The communication signal receiver coil is wound using 25 turns of AWG-38 magnet wire. These coils may be produced by respective windings around a suitably shaped former (not shown). The first coil winding 922 comprises a first plurality of wire loops and the second coil winding 924 comprises a second plurality of wire loops arranged in series with the first plurality of wire loops. The segmentation capacitor 930 is provided between the windings 922, 924. The inclusion of the segmentation capacitor 930 effectively reduces the coupling of the communication signal transmitter coil 920 and power signal transmitter coil 910 whilst still allowing an optimal size and number of windings for the communications coil. Furthermore, the segmentation capacitor 930 re-distributes the electrical field distribution between the coil windings, thereby reducing interwinding loss in the coil and improving its Q. A segmentation capacitor may similarly be utilised in the power signal transmitter coil 910 and/or in one or both of the receiver coils of any one of the inductive coil arrangements described and/or shown in this disclosure.

In FIGS. 14 and 15, the power signal transmitter coil 910 is a conformal printed spiral coil as in the embodiments of FIGS. 5, 6, 9, 10*a*, 11*a* and 13. The power signal transmitter coil 910 is manufactured as a flexible printed circuit board (about 8×6 mm) with spiral copper traces on top (7 turns) and on bottom layer (7 turns).

FIG. 15 shows an embodiment of a transmitter coil assembly and a receiver coil assembly for use in an earbud and in an implant respectively. The embodiment is a hybrid solenoid and spiral coil arrangement. The communication signal receiver coil 1020 and the power signal receiver coil 1010 are each arranged in a wire-wound rectangular solenoid arrangement that allows typical implantable device manufacturing materials and processes. The power signal receiver coil 1010 and the communication signal receiver coil 1020 are arranged orthogonal to each other to maximise the passive magnetic decoupling of the coils. This technique allows the coils to be optimised for coupling to their respective transmitter coils across the transcutaneous link, whilst passively decoupling power and communications at the implant side.

The communication signal transmitter coil 920 and the power signal transmitter coil 910 arrangement is a hybrid arrangement with a curved flat spiral power signal transmitter coil 910 for maximising the coil surface area and minimising distance to the power signal receiver coil 1020, whilst utilising a circular wound solenoid coil for the communication signal transmitter coil 920. The communication signal transmitter coil 920 is the coil of FIG. 14 and includes a segmentation capacitor 930 between two coil windings 922, 924. The hybrid arrangement of the inductive link has been found to significantly increase the magnetics efficiency of the inductive link over non-hybrid coil arrangements. The communication signal receiver coil 1020 has a length dimension d1. The first plurality of wire loops 922 and the second plurality of wire loops 924 of the communication signal transmitter coil 920 may be arranged at a distance d2 from one another that is approximately equal to or greater than the length dimension d1 of the communication signal receiving coil 1020, so that once the coils are in place in the ear canal and the implant respectively, the flux linkage between the two communication signal coils 920, 1020 may be maximised. Similarly, a length dimension d4 of the power signal receiver coil may be approximately equal to or greater than a length dimension d3 of the power signal transmitter coil. The relative sizing of the coils, including the distance d2 between windings 922, 924 of the communication signal transmitter coil 920, allows for optimum coupling of a transmitter coil with its respective receiver coil.

In a variation of this embodiment, a segmentation capacitor may also be utilised in the power signal transmitter coil 910 and/or one or both of the receiver coils 1010, 1020. In another variation, any one of the coils 910, 920, 1010, 1020 may include more than one segmentation capacitor. Whilst not specifically shown or described, any one of the power transmitter coils and the communication transmitter coils described and/or shown in this disclosure may include one or more segmentation capacitor. As discussed earlier in this disclosure, the inclusion of segmentation capacitors lowers the voltages in the system and the electric field around the coil is also lower. This means that there is less interaction between the coil and adjacent biological tissue. The presence of the biological tissue may affect the coil in two ways: (a) it leads to increased visible resistance of the coil, (b) it leads to change in the inductance of the coil, which may shift the resonance frequency. This potentially harmful behaviour depends on proximity and position of the tissue relative to the coil. Introducing tone or more segmentation capacitor can help minimise these issues.

The inductive link arrangement loops or windings may be made of copper. The number of loops/windings and the size of the wire or copper tracks will vary between individual coil designs as will be appreciated by the skilled person. In an example inductive coil arrangement such as that shown in FIG. 15, the power signal transmitter coil 910 may comprise of a 14 turn flexible printed circuit board planar coil utilising a copper trace. A segmentation capacitor, for example a 56 pF segmentation capacitor, may be utilised at the centre of the coil. The communication signal transmitter coil 920 may comprise a first plurality of wire loops 922 having 18 turns and a second plurality of wire loops 924 having 18 turns, totalling 36 turns of AWG-38 wire. The coil length may approximately 9.0 mm. A length dimension of each of the windings 922, 924 may be between 2 mm to 2.5 mm, for example 2.2 mm, such that the distance d2 is approximately 4.6 mm.

The power signal receiver coil 1010 may comprise a 10-turn AWG-34 coil and may include a 39 pF segmentation capacitor in a middle of the coil. The communication signal receiver coil 1020 may comprise a 25 turn AWG-38 coil. Useful dimensions may be derived from the dimensions of the transmitter coils, as described earlier.

Embodiments of the present invention are described with reference to the following non-limiting example.

Example 1

This example describes a coil design that has been built, the test procedure that is followed to measure its magnetics performance and the results obtained. The example demonstrates a coil design that has been found to have useful power and communication (data) transfer characteristics. The example also illustrates features that will influence these transfer characteristics.

Power Signal Transmitter (PTX) Coil and Communication Signal Transmitter (CTX) Coil The power signal transmitter coil was produced by etching 2 oz copper traces on a flexible printed circuit board in a spiral arrangement as shown in FIG. 16, with traces on top and bottom layers (7+7=14 turns in total). A 56 pF segmentation capacitor was provided in the middle of the coil.

The communication signal transmitter coil was made by winding copper wire around a cylindrical former/bobbin according to the following specification: 18+18=36 turns AWG-38 wire on a 2.7 mm diameter bobbin; length of the space available for the coil is 9.5 mm; actual length of the coil is 9.0 mm; and length of each of the two windings (18 turns each) is about 2.2 mm. FIG. 17a is a schematic illustrating the arrangement and FIG. 17b is a photograph of the communication signal transmitter coil as produced.

Figure 19:
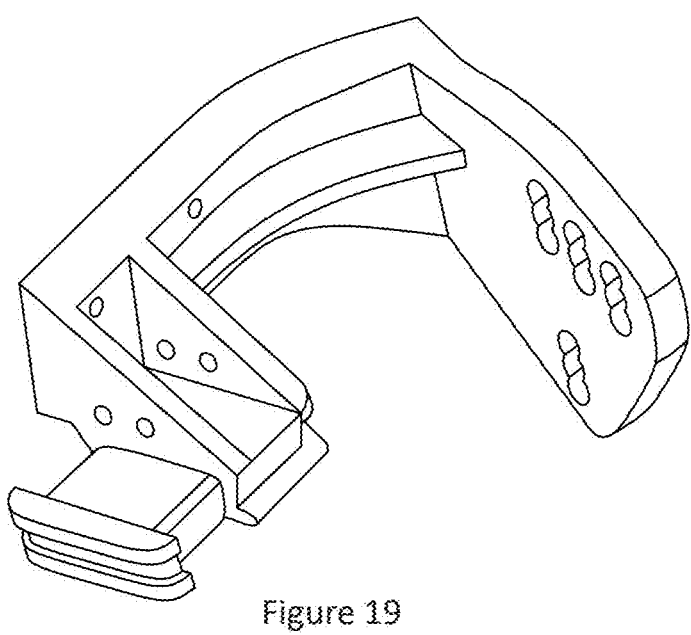
FIG. 19 shows a former useful for producing power signal receiver and communication signal receiver coils.

The flexible printed circuit board was suitably deformed to allow the power signal transmitter coil (1) to overlap the communication signal transmitter coil (2), as shown in FIG. 18. The arrangement is also as generally shown in FIG. 14. Power Signal Receiver (PRX) Coil and Communication Signal Receiver (CRX) Coil The former used to produce these coils was designed to allow each coil to be produced as a rectangular winding, with the coils arranged orthogonally to one another in an overlapping spatial relationship. The communication signal receiver coil is provided within the perimeter of the power signal receiver coil. The former used is shown in FIG. 19.

Figure 20:
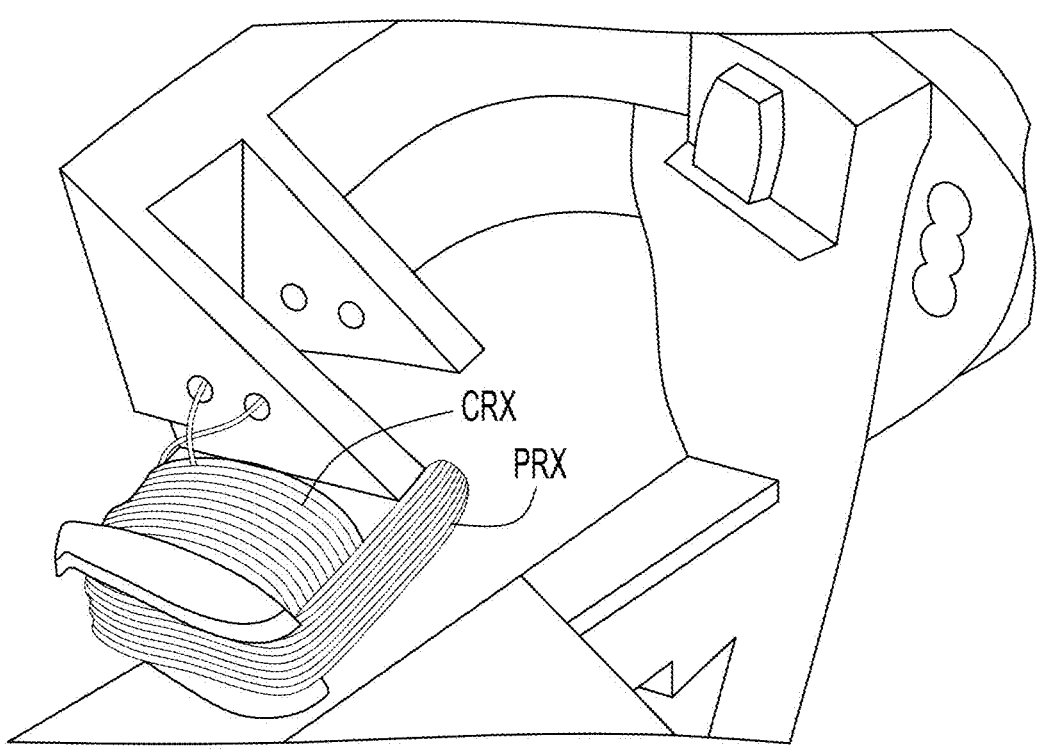
FIG. 20 shows power signal receiver and communication signal receiver coils provided on the former shown in FIG. 20.

The power receiver coil was produced by winding 10 turns of AWG-34 copper wire around a suitably shaped bobbin in a rectangular configuration, with each side of the rectangle being approximately 8.5 mm. A 39 pF segmentation capacitor was provided in the middle of the coil. The communication signal receiver coil was produced as a 25-turn AWG-38 coil using the same former, with each side of the rectangle being approximately 5 mm. The coils are arranged orthogonally to one another in an overlapping spatial relationship, with the communication signal receiver coil (CRX) positioned within the perimeter of the power signal receiver coil ((PRX) see FIG. 20). The arrangement is also generally as shown in FIG. 8. Suitable electrical connections are made to the various coils.

The transmitter coils and receiver coils are positioned relation to one another using a suitable test rig (not shown) that allows relative movement and positioning of the coil arrangements.

Figure 21:
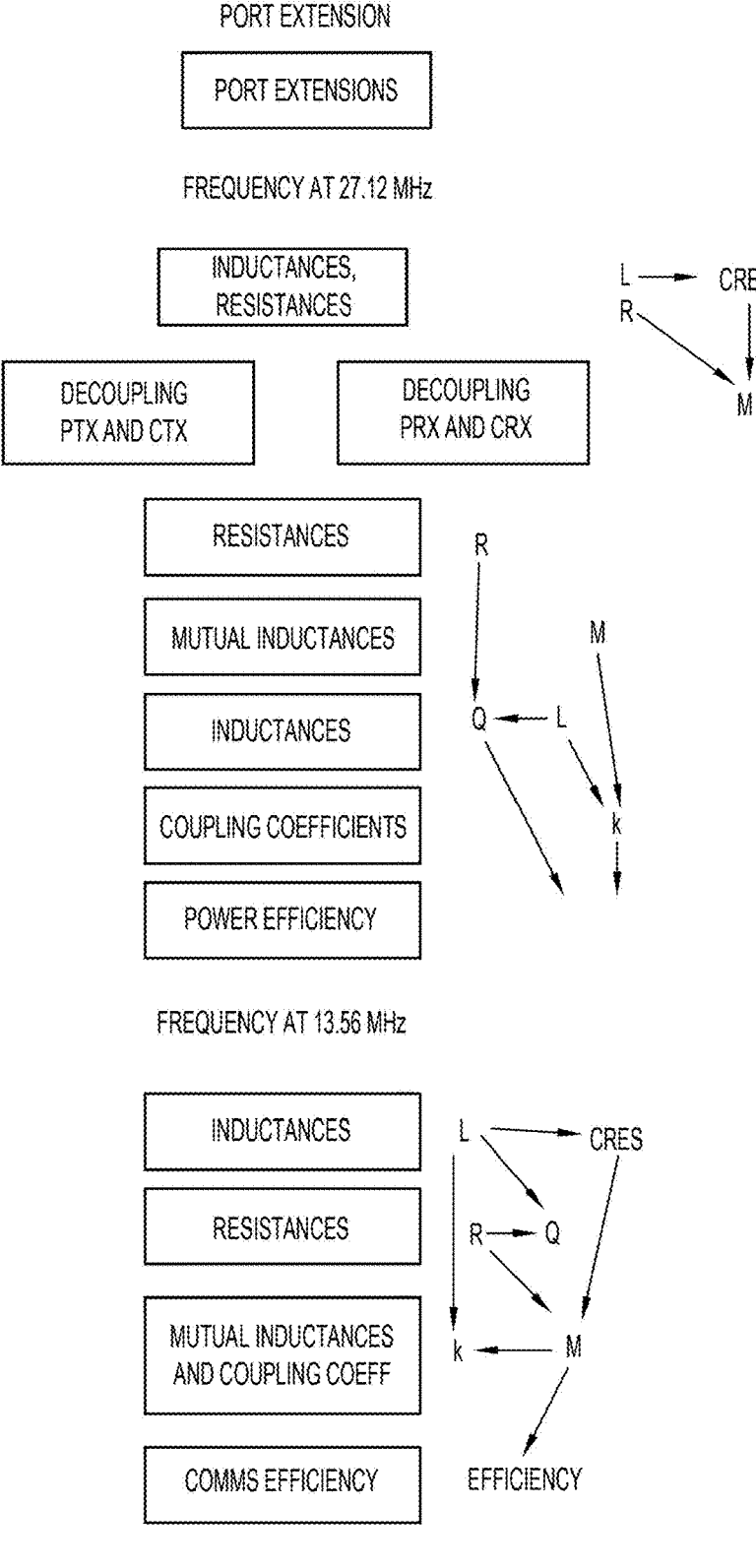
FIG. 21 is a chart depicting test protocol employed in the example.

FIG. 21 illustrates the testing protocols used.

Port Extension

Port 1 of a network analyser was calibrated from 10 MHz to 1 GHz. IFBW 1 kHz. A SMA connector was populated by 1 kOhm resistor. The port extension was adjusted to position data on the x-axis of a Smith chart. The value of the Port extension for the connector was recorded.

TABLE 1

| Connectors used in testing and port extension | |
| --- | --- |
| Connector/Cable | Port Extension, mm |
| SMA | 10 |

Characterising Coils at 27.12 MHz

Both ports of a network analyser were calibrated at a certain frequency (27.12 MHz or 13.56 MHz), span 2 MHz, IFBW 1 kHz.

Initial Resistances and Inductances

For PTX, the coil inductance was determined. The capacitance that resonates with the coil was calculated and appropriate capacitors soldered in series. The coil was connected to Port 1 of the network analyser. A Smith Chart was plotted. If necessary, the coil was fine-tuned (by replacing capacitors) to achieve R<ωL. The impedance Z was recorded. The resistance R=Re(Z) was determined.

For CTX, the coil inductance was determined. The capacitance that resonates with the coil was calculated and appropriate capacitors soldered in series. The coil was connected to Port 1 of the network analyser. A Smith Chart was plotted. If necessary, the coil was finetuned (by replacing capacitors) to achieve R<ωL. The impedance Z was recorded. The resistance R=Re(Z) was determined.

For PRX, the coil inductance was determined. The capacitance that resonates with the coil was calculated and appropriate capacitors soldered in series. The coil was connected to Port 1 of network analyser. A Smith Chart was plotted. If necessary, the coil was finetuned (by replacing capacitors) to achieve R<Im(Z). The impedance Z was recorded. The resistance R=Re(Z) was determined.

For CRX, the coil inductance was determined. The capacitance that resonates with the coil was calculated and appropriate capacitors soldered in series. The coil was connected to Port 1 of network analyser. A Smith Chart was plotted. If necessary, the coil was finetuned (by replacing capacitors) to achieve R<Im(Z). The impedance Z was recorded. The resistance R=Re(Z) was determined.

TABLE 2

| | Inductance L* as seen by network analyser, μH | Segmentation cap (if present), pF | Inductance L, μH | Resonance capacitors, pF | Measured impedance (with capacitor), Ω | Resistance, Ω |
|---|---|---|---|---|---|---|
| Coil | | | | | | |
| PTX | 0.49 | 56 | 1.10 | 68 + var (2-10) | 4.64 + j0.26 | 4.64 |
| CTX | 1.40 | | 1.40 | 20 + var (2-10) | 4.00 + j0.03 | 4.00 |
| PRX | 0.906 | 39 | 1.79 | 38 | 3.60 − j0.13 | 3.60 |
| CRX | 3.34 | | 3.34 | 4.7 + var (2-10) | 8.03 − j0.54 | 8.03 |

Initial inductances and resistances at 27.12 MHz

Note that we measure L' inductance, which is smaller than inductance of the coil, in case a segmentation capacitor is present.

Decoupling Transmitter Coils (PTX, CTX)

The PTX and CTX coils are located in close proximity to each other. This makes them very likely to be coupled with each other, which is unwanted. The coupling can be minimized by moving the CTX coil along the axis.

A SMA connector (with very short leads) was soldered to the PTX coil (still having capacitors on it.). The real part of impedance was measured with CTX being open $Re(Z_{open})$. The CTX coil (with capacitor and load resistor ~5 times larger than resistance of CTX coil) was shorted. The real part of impedance was measured with CTX being open $Re(Z_{short})$.

The position of the CTX coil was adjusted to bring the $Re(Z_{short})$ to a minimum, as close as possible to $Re(Z_{open})$. The following formula was used to calculate mutual inductance between the PTX and CTX coils. The coupling coefficient was also calculated.

$$M = \frac{1}{\omega}\sqrt{(R_{CTX} + R_L)\cdot(Re(Z_{short}) - Re(Z_{open}))}$$

TABLE 3

Mutual inductance and coupling coefficient for transmit coils at 27.12 MHz

| Coil pair | $Re(Z_{short})$, Ω | $Re(Z_{open})$, Ω | Load resistance, Ω | Mutual inductance, nH | Coupling coefficient |
|---|---|---|---|---|---|
| PTX (connected to NA) - CTX | 4.44 | 4.37 | 0 | 3.1 | 0.25% |

The mutual inductance and coupling coefficient are estimates, because the values of resistances and inductances may have slightly changed when adjusting the position of the coils.

The PTX and CTX coil have now been positioned such that their coupling is suitably low.

Decoupling Receiver Coils (PRX, CRX)

The PRX coil and CRX coil are wound on the same bobbin and located in close proximity to each other. This makes them very likely to be coupled with each other, which is unwanted. The coupling can be minimized by moving the wiring of the CRX coil. A SMA connector (with very short leads) is soldered to PRX coil (still having capacitors on it). The real part of impedance was measured with CRX being open $Re(Z_{open})$.

The CRX coil (with capacitor and load resistor ~5 times larger than resistance of CRX coil) was shorted. The real part of impedance with CRX being open $Re(Z_{short})$ was measured.

The position of wiring of the CRX coil was adjusted to bring the $Re(Z_{short})$ to a minimum, as close as possible $Re(Z_{open})$. The following formula was used to calculate mutual inductance between the PRX and CRX coil. The coupling coefficient was calculated.

$$M = \frac{1}{\omega}\sqrt{(R_{CRX} + R_L)\cdot(Re(Z_{short}) - Re(Z_{open}))}$$

TABLE 4

Mutual inductance and coupling coefficient for receive coils at 27.12 MHz

| Coil pair | $Re(Z_{short})$, $\Omega$ | $Re(Z_{open})$, $\Omega$ | Load resistance, $\Omega$ | Mutual inductance, nH | Coupling coefficient |
|---|---|---|---|---|---|
| PRX (connected to NA) - CRX | 3.60 | 3.60 | 0 | 0 | 0 |

The mutual inductance and coupling coefficient are estimates, because the values of resistances and inductances may have slightly changed when adjusting the position of the coils.

The PRX and CRX coils have now been positioned such that their coupling is at a minimum.

Resistances

With tuning capacitors in place the resistances of the four coils was determined. For each coil, the resistance was measured in the presence of the other coils.

TABLE 5

Resistances at 27.12 MHz

| Coil pair | Resistance, $\Omega$ |
|---|---|
| PTX | 4.34 |
| CTX | 4.00 |

TABLE 5-continued

Resistances at 27.12 MHz

| Coil pair | Resistance, $\Omega$ |
|---|---|
| PRX | 3.59 |
| CRX | 8.14 |

Mutual Inductances

Keeping the resonance capacitors in place. The following method may be used to determine the coupling coefficient.

The coils may be segmented or not. Display the S11 parameter on the Smith chart. Set marker to the target frequency. Plug the SMA connector with the first coil to Port 1 of a network analyser. Plug the SMA connector with the second coil to Port 2 of the network analyser. Save the data to S2P (Touchstone) file and optionally to CSV file. Open the S2P file, find the line containing S-parameters for the centre frequency. Move the S-parameter data to MATLAB. Convert the S-matrix to Z-matrix using the formula $Z=Z_0 (U+S)(U-S)^{-1}$ The mutual inductance can be calculated using the formula$=Im(Z_{21})/\omega$. The coupling coefficient can be calculated as $K=M/\sqrt{L_1 L_2}$

TABLE 6

Mutual inductance and coupling coefficient for six coil pairs at 27.12 MHz

| Coil pair | $Re(Z_{short})$, $\Omega$ | $Re(Z_{open})$, $\Omega$ | Load resistance, $\Omega$ | Mutual inductance, nH |
|---|---|---|---|---|
| PTX (connected to NA) - CTX | 4.46 | 4.37 | 0 | 1/omega*sqrt((4.46 − 4.37)*4.00) = 3.5 |
| PTX (connected to NA) - PRX | 11.73 | 4.35 | 18.7 | 1/omega*sqrt((11.73 − 4.35)*(3.59 + 18.7)) 75.2 |
| PTX (connected to NA) - CRX | 4.46 | 4.36 | 43.2 | 1/omega*sqrt((4.46 − 4.36)*(8.14 + 43.2)) 13.3 |
| CTX (connected to NA) - PRX | 4.02 | 4.00 | 18.7 | 1/omega*sqrt((4.02 − 4.00)*(3.59 + 18.7)) 3.9 |
| CTX (connected to NA) - CRX | 4.07 | 4.00 | 43.2 | 1/omega*sqrt((4.07 − 4.00)*(8.14 + 43.2)) 11.1 |
| PRX (connected to NA) - CRX | 3.60 | 3.60 | 43.2 | 1/omega*sqrt((4.60 − 4.60)*(8.14 + 43.2)) 0 |

Inductances

The tuning capacitors and load resistances were removed from the coils. SMA connectors are connected to each of the four coils (PTX, CTX, PRX, CRX) consecutively. For each coil, the coil inductance was measured as described in "Measuring coil inductance" section.

TABLE 7

| | Inductances at 27.12 MHz | | |
| --- | --- | --- | --- |
| Coil | Inductance L* as seen by network analyser, μH | Segmentation cap (if present), pF | Inductance L, μH | Quality factor |
| PTX | 0.49 | 56 | 1.10 | 43.2 |
| CTX | 1.40 | | 1.40 | 59.6 |
| PRX | 0.91 | 39 | 1.79 | 85.0 |
| CRX | 3.38 | | 3.38 | 70.7 |

Coupling Coefficients

With inductances and mutual inductances known the coupling coefficients were calculated.

TABLE 8

| Coupling coefficient for six coils at 27.12 MHz | |
| --- | --- |
| Coil pair | Coupling coefficient |
| PTX-CTX | 0.28% |
| PTX-PRX | 5.36% |
| PTX-CRX | 0.69% |
| CTX-PRX | 0.25% |
| CTX-CRX | 0.51% |
| PRX-CRX | 0% |

These results demonstrate the low coupling between the six sets of coils present in the system at 27.12 MHz.

Calculating Power Transfer Efficiency

The mutual quality factor was calculated using the formula:

$$Q_M = \frac{\omega M}{\sqrt{R_t R_r}} = k\sqrt{Q_t Q_r}$$

The maximum possible efficiency was calculated using the formula:

$$\eta = \frac{\sqrt{1 + Q_M^2} - 1}{\sqrt{1 + Q_M^2} + 1}$$

The optimal load resistance was calculated using the formula:

$$R_L = R_r\sqrt{1 + Q_M^2}$$

TABLE 9

| Mutual quality factor and efficiency for power coils at 27.12 MHz | | | |
| --- | --- | --- | --- |
| Coil pair | Mutual quality factor | Efficiency | Load resistance, Ω |
| PTX-PRX | 3.24 | 54.4% | 12.7 |

Characterizing Coils at 13.56 MHz

Both ports of the network analyser were calibrated at 13.56 MHz, span 2 MHz, IFBW 1 kHz.

Inductances and Resistances

A SMA connector was connected to each of the two coils (CTX, CRX) consecutively. For each coil, the coil inductance was measured. Having measured inductances of the two coils, the resonance capacitors for each of the two coils (CTX, CRX) was calculated. The resistances of the two coils were determined. For each coil, the resistance is measured in the presence of other coils. The quality factors were calculated from the values of inductances and resistances.

TABLE 10

| | Inductance and resistances for Comms coils at 13.56 MHz | | | | | | |
| --- | --- | --- | --- | --- | --- | --- | --- |
| Coil | Inductance L* as seen by network analyser, μH | Segmentation cap (if present), pF | Inductance L, μH | Resonance capacitors, pF | Measured impedance (with capacitor), Ω | Resistance, Ω | Quality factor |
| CTX | 1.38 | | 1.38 | 100 | 2.55 + j0.15 | 2.55 | 46.1 |
| CRX | 3.16 | | 3.16 | 43.6 | 4.11 − j0.08 | 4.11 | 65.5 |

Mutual Inductance and Coupling Coefficient

With the resonance capacitors in place the coupling coefficient between CTX and CRX was determined. Previously determined inductances were used to calculate coupling coefficients. It has been found that with resonance capacitors in place it may be possible to achieve comparable (or possibly improved) data transfer at reduced coupling factor. The resonance capacitor is believed to increase the coupling between the primary (communication signal transmission and secondary (communication signal receiver) coils.

TABLE 11

| | | | Load | Mutual | |
| | $Re(Z_{short})$, | $Re(Z_{open})$, | resistance, | inductance, | Coupling |
| Coil pair | $\Omega$ | $\Omega$ | $\Omega$ | nH | coefficient |
|---|---|---|---|---|---|
| CTX-CRX | 2.72 | 2.54 | 0 | 10.1 | 0.48% |

Mutual inductance and coupling coefficient for Comms coils at 13.56 MHz

Calculating Comms Efficiency

Voltage induced along the terminals of the Comms receive coil (CRX) is $$V = \omega M I$$

where M is mutual inductance between CTX and CRX coils.

The comms efficiency of the link is defined as voltage induced on the terminals of the receive coil per unit current flowing in the transmit coil.

Two separate cases were considered:

(a) Receiver coil is directly connected to the amplifier. In this case, $$V/I = \omega M = \omega k \sqrt{L_{CTX} L_{CRX}}$$

(b) Receiver coil is in resonance with shunt capacitor In this case, $$V/I = \omega M Q_{CRX} = \omega Q_{CRX} k \sqrt{L_{CTX} L_{CRX}}$$

which is $Q_{CRX}$ larger than in case of direct connection.

TABLE 12

Voltage induced in the Comms Receive coil per unit current at 13.56 MHz

| Coil pair | $V/I = \omega M$, V/A | $V/I = \omega M Q_{CRX}$, V/A |
|---|---|---|
| CTX-CRX | 0.86 | 56 |

Self-Resonance

Display S11-parameter on the Smith chart. With the SMA connectors in place one port of the network analyser was calibrated in the range 20-200 MHz, IFBW 1 kHz. For each of the four coils, the marker to the frequency was moved to where the plot is crossing the x-axis of the Smith chart near the high impedance point. This gives the self-resonance frequency of the corresponding coil. It will be noted that the operating frequencies employed (13.56 MHz and 27.12 MHz) are well below the reported self-resonance frequencies of the coils. Problems can arise if the operating frequency is close to the self-resonance frequency of one or more of the coils. In that case, it is possible to modulate the self-resonance frequency by inclusion of a shunt capacitor in the circuitry of the relevant coil(s).

TABLE 13

Self-resonance frequency

| Coil | Self-resonance frequency, MHz |
|---|---|
| PTX | 73.2 |
| CTX | 165 |

TABLE 13-continued

Self-resonance frequency

| Coil | Self-resonance frequency, MHz |
|---|---|
| PRX | 116 |
| CRX | 93 |

Embodiments of the inductive link arrangement described herein permit the inductive coil arrangement, and the sound processor, to be housed within an earbud for positioning in the ear canal of a patient. The ear canal has greater consistency of skin/tissue thickness between patients. The earbud removes the need for a locating magnet and its position within the ear canal is aesthetically pleasing for patients. Removing the magnet reduces the impact on MRI scans significantly.

Furthermore, embodiments of the inductive link arrangement described herein effectively decouple the power and communication links within the space constraints of the earbud or behind-the-ear transmitter coil arrangement and the implant, providing a high efficiency power link that is separate to the communications link and allowing for an effective forward and backward communications link, not only on the communications link, but also on the power link. Accordingly, the separate power and communications links of the disclosed inductive link arrangements permits a full-duplex communications link. The communications inductive link is for communicating audio/stimulation data to the implant. The data may be stimulation data and/or data relating to programming the implant with patient specific configuration data or for upgrading firmware in the implant. The backchannel communication across the communication link is for reading data from the implant, which is required when taking implant measurements for patients, e.g., voltage or impedance measurements of an individual so that a customised stimulation map may be created. It is also beneficial for taking implant diagnostic measurements.

The communication across the power link is beneficial for optimising in real time the implant power. The power backchannel communication link can be utilised to regulate the power/voltage being sent across the power link to the implant so that energy is not wasted in the system by transferring more power across the link than is necessary. This is beneficial as each patient will have different stimulation requirements. These differences, which can be from impedances in the cochlea, require patient specific current levels for the cochlea to be stimulated. Thus, each recipient will require different power requirements across the link. Having a feedback system for the power across the power link means that electronics within the earbud may vary the power transferred across the power link to optimise the cochlear implant system power, which in turn optimises the battery life of the cochlear implant system per patient.

Throughout this specification the word "comprises", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

The invention claimed is:

1. An inductive coil arrangement for delivering a power signal and a communication signal over a transcutaneous link, the inductive coil arrangement comprising:

a power signal transmitter coil for transmitting a power signal;

a communication signal transmitter coil for transmitting a communication signal, wherein the communication signal transmitter coil is magnetically decoupled from the power signal transmitter coil;

a power signal receiver coil for receiving the power signal from the power signal transmitter coil, wherein the power signal receiver coil is magnetically coupled to the power signal transmitter coil, but is magnetically decoupled from the communication signal transmitter coil; and a communication signal receiver coil for receiving the communication signal from the communication signal transmitter coil, wherein the communication signal receiver coil is magnetically coupled to the communication signal transmitter coil, but is magnetically decoupled from the power signal receiver coil, wherein the power signal transmitter coil is independent from the communication signal transmitter coil and the power signal receiver coil is independent from the communication signal receiver coil, and wherein, in use, delivery of the power signal over the transcutaneous link is independent of delivery of the communication signal over the transcutaneous link.

2. The inductive coil arrangement of claim 1, wherein the communication signal transmitter coil and the power signal transmitter coil are arranged in an at least partially overlapping spatial relationship.

3. The inductive coil arrangement of claim 2, wherein the power signal transmitter coil has a planar curved shape, and the communication signal transmitter coil has a generally cylindrical shape.

4. The inductive coil arrangement of claim 1, wherein respective receiver coils are planar coils arranged parallel to one another in a partially overlapping spatial relationship.

5. The inductive coil arrangement of claim 1, wherein the receiver coils are air-core coils arranged with respective central axes orthogonally to one another and in an overlapping spatial relationship, wherein the communication signal receiver coil is positioned within the perimeter defined by the power signal receiver coil, or the power signal receiver coil is positioned within the perimeter defined by the communication signal receiver coil.

6. The inductive coil arrangement of claim 1, wherein the communication signal transmitter coil and the power signal transmitter coil are arranged in an at least partially overlapping spatial relationship, and the central axis of the communication signal transmitter coil is substantially parallel to or tilted at an angle with respect to the central axis of the power signal transmitter coil.

7. The inductive coil arrangement of claim 6, wherein the communication signal transmitter coil is a circular planar coil and the power signal transmitter coil is a planar curved coil that has a curvature that complements a portion of the circumference of the circular communication signal transmitter coil to allow the power signal transmitter coil to overlap the communication signal transmitter coil at least partially.

8. The inductive coil arrangement of claim 6, wherein the angle may be varied to reduce coupling between the communication signal transmitter coil and the power signal transmitter coil.

9. The inductive coil arrangement of claim 7, wherein the longitudinal position of the planar communication signal transmitter coil along the length of the power transmitter coil may be varied to reduce coupling between the communication signal transmitter coil and the power signal transmitter coil.

10. The inductive coil arrangement of claim 1, wherein the power signal transmitter coil and/or the communication signal transmitter coil include one or more segmentation capacitors.

11. The inductive coil arrangement of claim 1, wherein the communication signal receiver coil and/or the power signal receiver coil include one or more segmentation capacitors.

12. The inductive coil arrangement of claim 1, wherein the communication signal transmitter coil comprises a first plurality of wire loops and a second plurality of wire loops arranged in series, and wherein the first plurality of wire loops and the second plurality of wire loops are capacitively coupled and arranged in a spaced relationship with one another.

13. The inductive coil arrangement of claim 1, wherein the power signal transmitter coil may be configured to transmit a power signal to the power signal receiver coil at a frequency that is approximately two to three times higher than a frequency at which the communication signal transmitter coil is configured to transmit the communication signal to the communication signal receiver coil.

14. The inductive coil arrangement of claim 1, wherein the power signal transmitter coil may be configured to transmit a power signal to the power signal receiver coil at a frequency that is separated by at least 10 MHz from the frequency at which the communication signal transmitter coil is configured to transmit a communication signal to the communication signal receiver coil.

15. An implantable medical system comprising an inductive coil arrangement as claimed in claim 1.

16. A cochlear implant system comprising an inductive coil arrangement as claimed in claim 1, wherein the system comprises an external sound processor comprising the power signal transmitter coil and the communication signal transmitter coil, and an implantable receiver/stimulator comprising the power signal receiver coil and the communication signal receiver coil.

17. A cochlear implant according to claim 16, wherein the sound processor takes the form of one of a) an earbud for insertion into an ear canal of a patient or b) a behind the ear component.

18. A method of transmitting a power signal and a communication signal independently over a transcutaneous link, the method comprising providing an inductive coil arrangement as claimed claim 1, and transmitting a power signal from the power signal transmitter coil to the power signal receiver coil and transmitting a communication signal from the communication signal transmitter coil to the communication signal receiver coil.

19. A method for delivering a power signal and a communication signal over a transcutaneous link using an inductive coil arrangement, the method comprising:

transmitting a power signal via a power signal transmitter coil;

transmitting a communication signal via a communication signal transmitter coil, wherein the communication signal transmitter coil is magnetically decoupled from the power signal transmitter coil;

receiving, at a power signal receiver coil, the power signal from the power signal transmitter coil, wherein the power signal receiver coil is magnetically coupled to the power signal transmitter coil, but is magnetically decoupled from the communication signal transmitter coil; and receiving, at a communication signal receiver coil, the communication signal from the communication signal transmitter coil, wherein the communication signal receiver coil is magnetically coupled to the communication signal transmitter coil, but is magnetically decoupled from the power signal receiver coil, wherein the power signal transmitter coil is independent from the communication signal transmitter coil and the power signal receiver coil is independent from the communication signal receiver coil, and wherein, in use, delivery of the power signal over the transcutaneous link is independent of delivery of the communication signal over the transcutaneous link.

20. The method of claim 19, wherein the communication signal transmitter coil and the power signal transmitter coil are arranged in an at least partially overlapping spatial relationship.

* * * * *